US008747870B2

(12) United States Patent
Gupta et al.

(10) Patent No.: US 8,747,870 B2
(45) Date of Patent: Jun. 10, 2014

(54) POLYMERIC COMPOSITIONS AND METHODS OF MAKING AND USING THEREOF

(71) Applicant: University of Utah Research Foundation, Salt Lake City, UT (US)

(72) Inventors: Kavita Gupta, Salt Lake City, UT (US); Meredith R. Clark, Bethesda, MD (US); Patrick F. Kiser, Chicago, IL (US); Julie I. Jay, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/742,877

(22) Filed: Jan. 16, 2013

(65) Prior Publication Data

US 2013/0129797 A1 May 23, 2013

Related U.S. Application Data

(63) Continuation of application No. 12/226,547, filed as application No. PCT/US2007/009797 on Apr. 20, 2007.

(60) Provisional application No. 60/793,682, filed on Apr. 20, 2006, provisional application No. 60/881,889, filed on Jan. 23, 2007.

(51) Int. Cl.

| | |
|---|---|
| ***A61K 9/00*** | (2006.01) |
| ***A61K 39/395*** | (2006.01) |
| ***A61K 47/32*** | (2006.01) |
| ***C08F 30/06*** | (2006.01) |
| ***C08F 130/06*** | (2006.01) |
| ***C08F 230/06*** | (2006.01) |

(52) U.S. Cl.
USPC .................... 424/400; 424/130.1; 514/772.4; 526/239

(58) Field of Classification Search
USPC ............. 424/400, 130.1; 514/772.4; 526/239
See application file for complete search history.

(56) References Cited

U.S. PATENT DOCUMENTS

| | | | | |
|---|---|---|---|---|
| 4,507,466 | A | 3/1985 | Tomalia et al. | 528/332 |
| 4,558,120 | A | 12/1985 | Tomalia et al. | 528/363 |
| 4,568,737 | A | 2/1986 | Tomalia et al. | 528/332 |
| 4,587,329 | A | 5/1986 | Tomalia et al. | 528/363 |
| 4,897,355 | A | 1/1990 | Eppstein et al. | 424/450 |
| 5,135,919 | A | 8/1992 | Folkman et al. | 514/56 |
| 5,290,807 | A | 3/1994 | Folkman et al. | 514/75 |
| 5,504,074 | A | 4/1996 | D'Amato et al. | 514/182 |
| 5,594,111 | A * | 1/1997 | Stolowitz | 530/391.1 |
| 5,626,863 | A | 5/1997 | Hubbell et al. | 424/426 |
| 5,639,725 | A | 6/1997 | O'Reilly et al. | 514/12 |
| 5,650,173 | A | 7/1997 | Ramstack et al. | 424/489 |
| 5,661,143 | A | 8/1997 | D'Amato et al. | 514/182 |
| 5,698,586 | A | 12/1997 | Kishimoto et al. | 514/475 |
| 5,733,876 | A | 3/1998 | O'Reilly et al. | 514/12 |
| 5,792,845 | A | 8/1998 | O'Reilly et al. | 536/23.1 |
| 5,817,343 | A | 10/1998 | Burke | 424/489 |
| 5,837,682 | A | 11/1998 | Folkman et al. | 514/12 |
| 5,837,752 | A | 11/1998 | Shastri et al. | 523/116 |
| 5,844,016 | A | 12/1998 | Sawhney et al. | 522/13 |
| 5,854,205 | A | 12/1998 | O'Reilly et al. | 514/2 |
| 5,854,221 | A | 12/1998 | Cao et al. | 514/12 |
| 5,861,372 | A | 1/1999 | Folkman et al. | 514/2 |
| 5,885,795 | A | 3/1999 | O'Reilly et al. | 423/69.1 |
| 5,892,069 | A | 4/1999 | D'Amato et al. | 552/627 |
| 5,902,599 | A | 5/1999 | Anseth et al. | 424/426 |
| 5,916,598 | A | 6/1999 | Rickey et al. | 424/501 |
| 5,945,403 | A | 8/1999 | Folkman et al. | 514/21 |
| 5,989,463 | A | 11/1999 | Tracy et al. | 264/4.1 |
| 6,017,954 | A | 1/2000 | Folkman et al. | 514/475 |
| 6,024,688 | A | 2/2000 | Folkman et al. | 514/12 |
| 6,051,248 | A | 4/2000 | Sawhney et al. | 424/426 |
| 6,086,865 | A | 7/2000 | Folkman et al. | 424/85.1 |
| 6,103,255 | A | 8/2000 | Levene et al. | 424/426 |
| 6,110,503 | A | 8/2000 | Rickey et al. | 424/501 |
| 6,153,211 | A | 11/2000 | Hubbell et al. | 424/426 |
| 6,156,884 | A | 12/2000 | Ahlem et al. | 530/391.1 |
| 6,174,861 | B1 | 1/2001 | O'Reilly et al. | 514/12 |
| 6,183,781 | B1 | 2/2001 | Burke | 424/486 |
| 6,201,065 | B1 | 3/2001 | Pathak et al. | 525/90 |
| 6,201,072 | B1 | 3/2001 | Rathi et al. | 525/415 |
| 6,521,223 | B1 | 2/2003 | Calias et al. | 424/78.08 |
| 6,534,591 | B2 | 3/2003 | Rhee et al. | 525/54.1 |

(Continued)

FOREIGN PATENT DOCUMENTS

| | | |
|---|---|---|
| WO | WO 98/05629 | 2/1998 |
| WO | WO 2007/124132 | 1/2007 |

OTHER PUBLICATIONS

Aggeli et al., "Responsive gels formed by the spontaneous self-assembly of peptides into polymeric beta-sheet tapes," *Nature* 386:259-262 (1997).

Balazs et al., "Rheological properties and biological function of hyaluronic acid," *Chem Mol Biol Intercel Matrix, Advan Study Inst* 3:1241-1253 (1970).

(Continued)

*Primary Examiner* — Gina C Justice
*Assistant Examiner* — Genevieve S Alley
(74) *Attorney, Agent, or Firm* — Ballard Spahr LLP

(57) ABSTRACT

Described herein are polymeric compositions that comprise at least one polymer residue and at least one crosslinking moiety, wherein the polymer residue is crosslinked by the crosslinking moiety and wherein the crosslinking moiety is formed from a reaction between a boronic acid moiety and a hydroxamic acid moiety. Also, described are methods of making and using such polymeric compositions.

24 Claims, 8 Drawing Sheets

(56) References Cited

U.S. PATENT DOCUMENTS

| | | | | |
|---|---|---|---|---|
| 6,548,081 | B2 | 4/2003 | Sadozai et al. | 424/426 |
| 6,551,610 | B2 | 4/2003 | Shalaby et al. | 424/426 |
| 2001/0049438 | A1 | 12/2001 | Dix et al. | 536/25.4 |
| 2002/0032202 | A1 | 3/2002 | Kikuchi et al. | 514/250 |
| 2002/0038004 | A1 | 3/2002 | Stolowitz et al. | 530/399 |
| 2002/0192722 | A1 | 12/2002 | Stolowitz et al. | 435/7.9 |
| 2003/0003018 | A1 | 1/2003 | Stolowitz et al. | 422/82.05 |
| 2003/0105280 | A1 | 6/2003 | Ahlem et al. | 530/330 |
| 2003/0180247 | A1 | 9/2003 | Morelli et al. | 424/70.24 |
| 2004/0072203 | A1 | 4/2004 | Dix et al. | 435/6 |
| 2005/0164402 | A1 | 7/2005 | Belisle et al. | 436/174 |
| 2006/0003900 | A1 | 1/2006 | Hanes et al. | 507/203 |
| 2006/0061288 | A1 | 3/2006 | Zwanenburg et al. | 315/149 |
| 2010/0285094 | A1 | 11/2010 | Gupta | |

OTHER PUBLICATIONS

Boeseken, "The use of boric acid for the determination of the configuration of carbohydrates," *Advs Carbohydrate Chem* (*Academic Press Inc*., New York, N.Y.) 4:189-210 (1949).

Brigham et al., *Am J Resp Cell Mol Biol* 1:95-100 (1989).

Bucci et al., "Boron(3+)/polysaccharide gels: influence of crosslink chemistry on rheological properties," *Polymer Preprints* 32:457-458 (1991).

Chujo et al., "Reversible gelation of polyoxazoline by means of Diels-Alder reaction," *Macromolecules* 23:2636-2641 (1990).

Felgner et al., *Proc Natl Acad Sci USA* 84:7413-7417 (1987).

Franse, M. W. C. P. in *Polymer Materials and Engineering* 142 (Delft University of Technology, Delft, The Netherlands, 2002).

Gibbs et al., "Rheology of hyaluronic acid," *Biopolymers* 6:777-791 (1968).

Lin et al., "Mechanical properties of a reversible, DNA-crosslinked polyacrylamide hydrogel," *J Biomech Eng* 126:104-110 (2004).

Liu et al., "Thermally reversible cross-linked polyamides and thermo-responsive gels by means of Diels-Alder reaction," *Polymer* 47:2581-2586 (2006).

Lorand et al., "Polyol complexes and structure of the benzeneboronate ion," *J Org Chem* 24:769-774 (1959).

Lutolf et al., "Synthesis and physicochemical characterization of end-linked poly(ethylene glycol)-co-peptide hydrogels formed by Michael-type addition," *Biomacromolecules* 4:713-722 (2003).

Moffatt et al., "PEGylated J591 mAb loaded in PLGA-PEG-PLGA tri-block copolymer for targeted delivery," *International Journal of Pharmaceutics* 317: 10-13 (2006).

Moffatt et al., "Tumor-specific gene delivery mediated by a novel peptide-polyethylenimine-DNA polyplex targeting aminopeptidase N/CD13," *Hum Gene Ther* 16:57-67 (2005).

Nowak et al., "Rapidly recovering hydrogel scaffolds from self-assembling diblock copolypeptide amphiphiles," *Nature* (London, United Kingdom) 417: 424-428 (2002).

Opsteen, J. A.; van Hest, J. C. M. *Chemical Comm* 57-59 (2005).

Parrish et al., "PEG- and peptide-grafted aliphatic polyesters by Click Chemistry," *J Am Chem Soc* 127:7404-7410 (2005).

Pearson et al., "Rheology of mucin," *Methods Mol Bio* 125:99-109 (2000).

Petka et al., "Reversible hydrogels from self-assembling artificial proteins," *Science* 281:389-392 (1998).

Pezron et al., "Reversible gel formation induced by ion complexation. 1. Borax-galactomannan interactions," *Macromolecules* 21:1121-1125 (1988).

Rogers et al., "Use of a novel cross-linking method to modify adenovirus topism," *Gene Therapy*, 4(12):1387-1392 (1997).

Schultz et al., "Chemorheology of poly(vinyl alcohol)-borate gels," *Macromolecules* 2:281-285 (1969).

Shu et al., "Disulfide cross-linked hyaluronan hydrogels," *Biomacromolecules* 3: 1304-1311 (2002).

Shung et al., "Crosslinking characteristics of and cell adhesion to an injectable poly(propylene fumarate-co-ethylene glycol) hydrogel using a water-soluble crosslinking system," *Tissue Eng* 9:243-254 (2003).

Sijbesma et al., "Reversible polymers formed from self-complementary monomers using quadruple hydrogen bonding," *Science* 278:1601-1604 (1997).

Stolowitz et al., "Phenylboronic acid-salicylhydroxamic acid bioconjugates. 1. A novel boronic acid complex for protein immobilization," *Bioconjugate Chemistry* 12:229-239 (2001).

Sugihara et al., "Cyclic benzeneboronate esters," *J Am Chem Soc* 80:2443-2446 (1958).

Tamura et al., "Highly selective and orally active inhibitors of Type IV collagenase (MMP-9 and MMP-2): N-sulfonylamino acid derivatives," *J Med Chem* 41:640-649 (1998).

Wang et al., "Hybrid hydrogels assembled from synthetic polymers and coiled-coil protein domains," *Nature* 397:417-420 (1999).

Wiley et al., "Phenylboronic Acid-Salicylhydroxamic Acid Bioconjugates. 2. Polyvalent Immobilization of Protein Ligands for Affinity Chromatography," *Bioconjugate Chemistry* 12:240-250 (2001).

Notice of Abandonment issued on Feb. 1, 2013 for U.S. Appl. No. 12/266,547, filed Jun. 18, 2009 (Applicant—Univ. of Utah Research Foundation; Inventors—Gupta, et al.;) (2 pages).

Final Rejection issued on Jul 17, 2012 for U.S. Appl. No. 12/226,547, filed Jun. 18, 2009 (Applicant—Univ. of Utah Research Foundation; Inventors—Gupta et al.;) (7 pages).

Response to Non-Final Rejection filed on Mar. 1, 2012 for U.S. Appl. No. 12/226,547, filed Jun. 18, 2009 (Applicant—Univ. of Utah Research Foundation; Inventors—Gupta et al.;) (8 pages).

Non-Final Rejection issued on Sep. 1, 2011 for U.S. Appl. No. 12/226,547, filed Jun. 18, 2009 (Applicant—Univ. of Utah Research Foundation; Inventors—Gupta et al.;) (8 pages).

Response to Restriction Requirement and Species Election filed on Jul. 6, 2011 for U.S. Appl. No. 12/226,547, filed Jun. 18, 2009 (Applicant—Univ. of Utah Research Foundation; Inventors—Gupta et al.;) (8 pages).

Requirement for Restriction/Election issued on Jun. 6, 2011 for U.S. Appl. No. 12/226,547, filed Jun. 18, 2009 (Applicant—Univ. of Utah Research Foundation; Inventors—Gupta et al.;) (10 pages).

Second Preliminary Amendment filed on Nov. 23, 2010 for U.S. Appl. No. 12/226,547, filed Jun. 18, 2009 (Applicant—Univ. of Utah Research Foundation; Inventors—Gupta et al.;) (9 pages).

Preliminary Amendment filed on Oct. 20, 2008 for U.S. Appl. No. 12/226,547, filed Jun. 18, 2009 (Applicant—Univ. of Utah Research Foundation; Inventors—Gupta et al.;) (4 pages).

Extended European search report issued on Mar. 7, 2002 for European Application No. 07755883.1, which claims priority to PCT/US2007/009797 filed on Apr. 20, 2006. (Applicant—University of Utah Research Foundation // Inventors—Gupta et al.) (3 pages).

International Preliminary Report on Patentability issued by the International Searching Authority on Oct. 22, 2008 for PCT/US2007/09797 filed on Apr. 20, 2007 and published as WO 2007/124132 on Jan. 11, 2007 (Applicant—University of Utah Research Foundation // Inventors—Gupta et al.) (6 pages).

International Search Report mailed by the International Searching Authority on Aug. 11, 2008 for PCT/US2007/09797 filed on Apr. 20, 2007 and published as WO 2007/124132 on Jan. 11, 2007 (Applicant—University of Utah Research Foundation // Inventors—Gupta et al.) (9 pages).

Written Opinion mailed by the International Searching Authority on Aug. 11, 2008 2008 for PCT/uS2007/09797 filed on Apr. 20, 2007 and published as WO 2007/124132 on Jan. 11, 2007 (Applicant—University of Utah Research Foundation // Inventors—Gupta et al.) (5 pages).

* cited by examiner

POLYMERIC COMPOSITIONS AND METHODS OF MAKING AND USING THEREOF

CROSS-REFERENCE TO RELATED APPLICATIONS

This application is a continuation of U.S. Nonprovisional application Ser. No. 12/226,547, filed on Jun. 18, 2009, which is a national stage filing of PCT/US07/09797, filed on Apr. 20, 2007, which application claims the benefit of priority to U.S. Provisional Application 60/793,682, filed on Apr. 20, 2006, and U.S. Provisional Application 60/881,889, filed on Jan. 23, 2007, which are both incorporated herein in their entireties by this reference.

ACKNOWLEDGEMENTS

The research leading to this invention was funded in part by the National Institutes of Health, grant NIH-NIAID R21AI62445-01. The U.S. Government has certain rights in this invention.

BACKGROUND

Polymeric compositions are widely used in medical applications. For example, various polymers have been used as suture materials and for fracture fixation (see e.g., U.S. Pat. Nos. 5,902,599 and 5,837,752). Polymers have also been used in polymer-based drug delivery systems. For drug delivery, polymers are typically used as a matrix for the controlled or sustained release of biologically active agents. Examples of such polymer-based drug delivery systems are described in, for example, U.S. Pat. Nos. 6,183,781, 6,110,503, 5,989,463, 5,916,598, 5,817,343, and 5,650,173. Polymers have also been used as scaffolds for tissue engineering (see e.g., U.S. Pat. No. 6,103,255). Additionally, polymers have been used in dental applications as adhesives and fillers (see e.g., U.S. Pat. No. 5,902,599).

One type of polymeric composition that has received considerable attention for medical applications is the hydrogel. Hydrogels are three-dimensional polymer networks composed of homopolymers or copolymers that are capable of absorbing large amounts of water. Thus, a characteristic of hydrogels is that they swell in water or aqueous fluids without dissolving. High water content and soft consistency make hydrogels similar to natural living tissue more than any other class of synthetic biomaterials. Accordingly, many hydrogels are compatible with living systems and hydrogels have found numerous applications in medical and pharmaceutical industries. For example, hydrogels have been investigated widely as drug carriers due to their adjustable swelling capacities, which permit flexible control of drug release rates.

Under certain situations, it may be desirable to prepare a polymeric composition such as a hydrogel at the site of its intended use. However, a disadvantage of some polymeric compositions is that the polymers must be formed before they can be used. This is because the preparation of many types of polymers typically requires extreme conditions that are not compatible with the environment that the polymeric composition is intended to be used in (e.g., uses in biological systems). For example, the preparation of some polymers can require high temperature, exotic reagents, initiators, and/or solvents, and expensive and/or toxic catalysts. Another reason for preparing a polymeric composition before it can be used is that polymers are typically prepared from reactive monomers or oligomers, which, instead of forming the desired polymer network, can react with cells, tissues, biomolecules, and other species present in a given application.

Similar problems also exist when using polymeric compositions that require crosslinking, which is the formation of a linkage (e.g., covalent, non-covalent, or combinations thereof) between polymer chains or between portions of the same polymer chain. Crosslinking is frequently accomplished through the introduction of a crosslinker that has functionality capable of reacting chemically with functionality on one or more polymer chains. Crosslinking is often done to provide rigidity to the polymer system. For hydrogels, the polymer network is created by forming crosslinks between polymeric chains. For many polymeric compositions, extreme conditions and reactive crosslinkers are required for crosslinking. And as discussed above, such conditions are not generally compatible with certain environments (e.g., biological systems). Thus, crosslinking is often performed prior to using a polymer composition in a given application.

It can be desirable in certain applications to have crosslinking that is reversible, e.g., one or more crosslinks can be formed, broken, and reformed in the same or different location in the polymer network. Gels that dynamically restructure are commonly observed in nature, including synovial fluid (Balazs and Gibbs, *Chem Mol Biol Intercell Matrix, Advan Study Inst* 3:1241-53, 1970; Gibbs et al., *Biopolymers* 6:777-91, 1968) and mucins (Pearson et al., *Methods in Molecular Biology,* 125:99-109, 2000). Such materials are the subject of intense investigation for fundamental material science and advanced biomaterial applications, such as artificial biofluids and biosolids, cell encapsulation, tissue engineering and injectable drug delivery. The balance of solid-like and fluid-like behavior within such a gel typically results from the chemical equilibrium of reversible crosslinking interactions between polymer chains (Franse, *Polymer Materials and Engineering* 142, 2002; Goodwin et al., *Rheology for Chemists: An Introduction,* 2000). Contemporary research on viscoelastic gels focuses on exploiting hydrogen bonding interactions in protein-based networks or other self-assembled systems (Aggeli et al., *Nature* 386:259-62, 1997; Nowak et al., *Nature* 417:424-28, 2002; Sijbesma et al., *Science* 278:1601-04, 1997; Wang et al., *Nature* 397:417-20, 1999; Lin et al., *J Biomech Eng* 126:104-10, 2004; Petka et al., *Science* 281:389-92, 1998). Reversible covalent crosslinks (Boeseken, *Adv Carbohydrate Chem* 4:189-210, 1949; Lorand and Edwards, *J Org Chem* 24:769-74, 1959; Sugihara and Bowman, *J Am Chem Soc* 80:2443-46, 1958), on the other hand, could provide an energetically favorable, specific and controlled mechanism for engineering the viscoelasticity of gel networks (Bucci et al., *Polymer Preprints* 32:457-8, 1991; Pezron et al., *Macromolecules* 21:1121-5, 1988; Schultz and Myers, *Macromolecules* 2:281-85, 1969).

The wide variety of medical applications for polymeric compositions demonstrates the need for the development of different types of compositions with varying physical properties for use in various applications (e.g., medical applications). Further it would be desirable in some instances to have polymeric compositions that can be prepared or crosslinked in situ in a biological environment under mild conditions. Still further, it would be desirable in some instances to have polymeric compositions that can change their viscoelastic properties under certain conditions. The subject matter disclosed herein meets these and other needs.

SUMMARY

In accordance with the purposes of the disclosed materials, compounds, compositions, articles, devices, and methods, as embodied and broadly described herein, the disclosed subject matter, in one aspect, relates to compounds and compositions and methods for preparing and using such compounds and compositions. In a further aspect, disclosed herein are polymeric compositions that comprise at least one polymer residue and at least one crosslinking moiety, wherein the polymer residue is crosslinked by the crosslinking moiety. In still a further aspect, disclosed herein are methods of making and using such polymeric compositions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 5A illustrates that covalent bonds forming between polymer-bound phenylboronic acid (PBA) and salicylhydroxamic acid (SHA) have pH-dependent binding equilibriums where bonds are highly reversible under acidic conditions. FIG. 5B illustrates linear water-soluble polymers containing either phenylboronic acid or salicylhydroxamic acid moieties can be synthesized with different polymer backbones (e.g., 2-hydroxypropylmethacrylamide (HPMA) or acrylic acid (AA)) of controlled molar feed ratios (x:(100−x) and y:(100−y)). FIG. 5C illustrates that when PBA- and SHA-containing polymer solutions are mixed under physiological conditions a reversible semisolid gel can form due to the dynamic restructuring of the crosslinked gel network. The specific pH range at which gels behave reversibly can be controlled with choice of polymer backbone (in 5B); HPMA-based PBA-SHA crosslinked gels are reversible at mildly acidic (pH 4-5) pH while AA-based PBA-SHA crosslinked gels are reversible at neutral pH.

FIG. 6A shows that oscillatory frequency sweeps of HPMA-based gels at pH 4.2 demonstrate frequency-dependent elastic (G') and viscous (G") moduli. G' (filled symbols) and G" (open symbols) of 1:1 mixtures of p(HPMA90-PBA10) and p(HPMA90-SHA10) at 25° C. of two different concentrations: 50 mg/mL (▲) or 100 mg/mL (■). The crossover between G' and G" for both gel concentrations was approximately 1 rad/s. Moduli increased with polymer concentration. FIG. 6B shows oscillatory frequency sweeps of PBA-SHA crosslinked gels at pH 7.6 demonstrate frequency-dependent G' and G" for AA-based gels but not HPMA-based gels. G' (filled symbols) and G" (open symbols) at 25° C. of 50 mg/mL gels comprised of either a 1:1 mixture of p(HPMA90-PBA10) and p(HPMA90-SHA10) (▲) or a 1:1 mixture of p(AA90-PBA10) and p(AA90-SHA10) (●). A crossover between G' and G" was observed for AA-based gels at approximately 0.6 rad/s, whereas HPMA-based gels showed G'>G" over the same experimental range. FIG. 6C shows reversible PBA-SHA crosslinked gels demonstrate rapid or slow self-healing post-fracture. Recovery of gel strength, G', for: pH 4.2 gels comprised of 1:1 mixtures of p(HPMA90-PBA10) and p(HPMA90-SHA10) at 75 mg/mL (♦) and 100 mg/mL (■); pH 7.6 gels comprised of 1:1 mixtures of p(AA90-PBA10) and p(AA90-SHA10) at 50 mg/mL (●). Failure was induced by large amplitude oscillatory stress (>10,000 Pa; 10-50 rad/s; 25° C.; 1 min) and recovery was observed over time during a small amplitude oscillatory stress period (5-50 Pa; 10-50 rad/s; 25° C.; 60 min). G' is normalized to the pre-failure gel strength, $G'_o$ (5-50 Pa; 10-50 rad/s; 25° C.) to facilitate comparison of samples with different gel strengths. FIG. 6D shows HPMA-based PBA-SHA crosslinked gels lose gel strength with slight temperature increase at pH 4.2 but not at pH 7.6. Percent change in gel strength, ΔG', at 37° C. as compared to initial gel strength at 25° C. of HPMA-based PBA-SHA crosslinked gels of varying polymer concentrations (light grey: 50 mg/mL, medium grey: 75 mg/mL; dark grey: 100 mg/mL) at pH 4.2 and 7.6. G'data was collected and averaged from the quasi-plateau region of oscillatory frequency sweep experiments performed at 25 and 37° C. for each sample. All experiments are represented as the means (±s.d. for d) of triplicate gel samples.

FIG. 8A is a photograph of an aqueous solution of p($HPMA_{90}$-$SHA_{10}$) at 50 mg/mL. FIG. 8B is a photograph of an aqueous solution of p($HPMA_{90}$-

$PBA_{10}$) at 50 mg/mL. FIG. 8C is a photograph showing gels of p($HPMA_{90}$-$SHA_{10}$) (8A) and p($HPMA_{90}$-$PBA_{10}$) (8B) mixed 1:1 at pH 4.2 that slowly flow following inversion due to the dynamic restructuring of the gel's reversible crosslinks. FIG. 8D is a photograph showing gels of p($HPMA_{90}$-$SHA_{10}$) (8A) and p($HPMA_{90}$-$PBA_{10}$) (8B) mixed 1:1 at pH 7.6 due not flow when inverted because the crosslinks have shifted to a more irreversibly crosslinked state. The schematic representation of these photographs is shown in FIG. 7.

DETAILED DESCRIPTION

Figure 1:
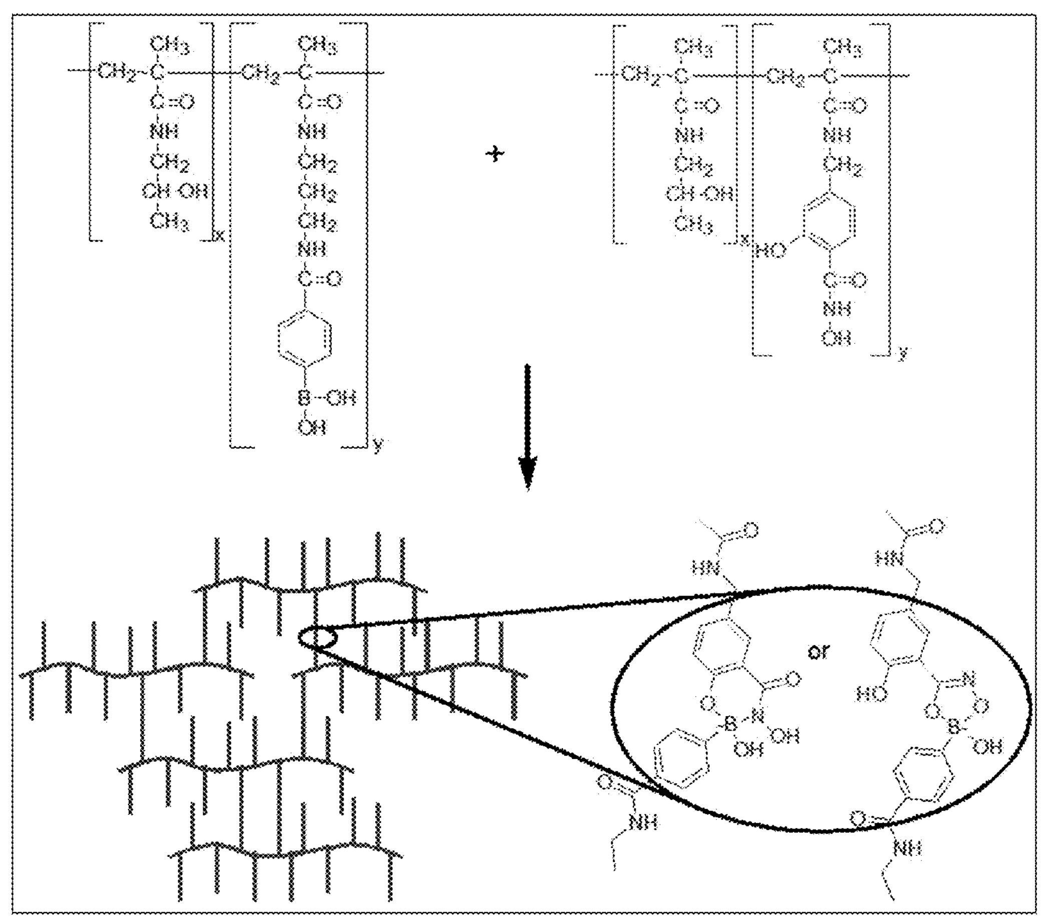
FIG. 1 is a schematic of hydrogel formation using boronic acid-hydroxamic acid crosslinking chemistry. Shown in the figure is a crosslinked hydrogel, which can be formed in water using a phenylboronic acid-functionalized hydrophilic polymer and a salicylhydroxamic acid-functionalized hydrophilic polymer. The expanded view illustrates the two different types of linkages that can be obtained with such functionalized polymers.

The materials, compounds, compositions, articles, devices, and methods described herein may be understood more readily by reference to the following detailed description of specific aspects of the disclosed subject matter and the Examples included therein and to the Figures.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

DEFINITIONS

In this specification and in the claims that follow, reference will be made to a number of terms that shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the polymer" includes mixtures of two or more such polymers, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

A "residue" of a chemical species, as used in the specification and concluding claims, refers to the moiety that is the resulting product of the chemical species in a particular reaction scheme or subsequent formulation or chemical product, regardless of whether the moiety is actually obtained from the chemical species.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol, as described herein. A "lower alkyl" group is an alkyl group containing from one to six carbon atoms.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The term "alkoxy" as used herein is an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1\text{-}(OA^2)_a\text{-}OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol, as described herein.

The term "cycloalkynyl" as used herein is a non-aromatic carbon-based ring composed of at least seven carbon atoms and containing at least one carbon-carbon tripple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "boronic acid" as used herein is represented by the formula $\text{-}A^1B(OH)_2$, where $A^1$ can be a substituted or unsubstituted alkyl, cycloalkyl, alkenyl, cycloalkenyl, alkynyl, cycloalkynyl, aryl, or heteroaryl group as described herein. Also included within the meaning of this term are ionized compounds, salts, and tetravalent structures.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The terms "hydroxamate" or "hydroxamic acid" as used herein are represented by the formula -$A^1$C(O)NHO$A^2$-, where $A^1$ can be a substituted or unsubstituted alkyl, cycloalkyl, alkenyl, cycloalkenyl, alkynyl, cycloalkynyl, aryl, or heteroaryl group as described herein, and $A^2$ can be a hydrogen or an alkyl group described herein.

The term "hydroxyl" as used herein is represented by the formula —OH.

The term "ketone" as used herein is represented by the formula $A^1$C(O)$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, S(O)$_2A^1$, —OS(O)$_2A^1$, or —OS(O)$_2$O$A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^{1\prime}$," "$R^2$," "$R^{2\prime}$," "$R^n$," "$R^{n\prime}$," "L," "L′," "X," "Y," and "Z" as used herein can, independently, possess one or more of the groups listed above. For example, if $R^{1\prime}$ is a polyether group, one of the hydrogen atoms of the polyether group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "a polyether group comprising an alkene group," the alkene group can be incorporated within the backbone of the polyether group. Alternatively, the alkene group can be attached to the backbone of the polyether group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components or moieties A, B, and C are disclosed as well as a class of components or moieties D, E, and F and an example of a composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Polymeric Compositions

In one aspect, disclosed herein are polymeric compositions that comprise at least one polymer residue and at least one crosslinking moiety, wherein the polymer residue is crosslinked by the crosslinking moiety and wherein the crosslinking moiety is formed from a reaction between a boronic acid moiety and a hydroxamic acid moiety. The disclosed polymeric compositions can be prepared in situ under mild aqueous conditions, as is described herein. For example, two (or more) liquid-state polymers (sometimes called "prepolymers" herein) can be mixed together under mild aqueous conditions to form a gel at room temperature and/or body temperature. The chemistry typically involves mixing an aqueous solution of polymers functionalized with one or more boronic acid moieties with a second aqueous solution of polymers functionalized with one or more hydroxamic acid moieties, forming covalently-bonded boronate esters between the two polymer residues. This crosslinking chemistry is rapid and stable under most physiological conditions (e.g., pH≥4 and ≥7). Also, while formation of the disclosed compositions (e.g., hydrogel formation) can be reversed under certain acidic conditions, crosslinking (gelation) is recoverable when pH is back-adjusted and/or temperature is adjusted. Furthermore, the crosslinked compositions disclosed herein can exhibit shear thinning properties as well as recovery of original viscoelastic behavior following removal of applied shear.

Also, disclosed herein are polymeric compositions that comprise hydrogel networks that form at physiological pH by the covalent yet reversible interactions of polymer-bound boronic acid moieties and hydroxamic acid moieties. These compositions can demonstrate pH-dependent viscoelastic behavior that can be controlled by, for example, the chemical composition of the polymer backbone. Moreover, the reversible crosslinks permit these compositions to restructure dynamically and self-heal following mechanical fracture. Compositions of this type provide a new and completely synthetic class of materials that allow unique control over their viscoelastic properties.

The polymeric compositions and methods disclosed herein provide certain advantages over other hydrogel systems, including, for example, synthetic ease over artificial protein (Wang et al., *Nature* 397:417-20, 1999; Petka et al., *Science* 281:389-92, 1998), peptide (Aggeli et al., *Nature* 386:259-62, 1997; Nowak et al., *Nature* 417:424-428, 2002; Sijbesma et al., *Science* 278:1601-04, 1997) and DNA (Lin et al., *J Biomech Eng* 126:104-10, 2004) based gels and improved functional group stability and controllable crosslinking as compared to thiol- and vinyl-based in situ gelling networks (Chujo et al., *Macromolecules* 23:2636-41, 1990; Liu et al., *Polymer* 47:2581-86, 2006; Lutolf and Hubbell, *Biomacromolecules* 4:713-22, 2003; Shu et al., *Biomacromolecules* 3:1304-11, 2002; Shung et al., *Tissue Eng* 9:243-54, 2003). And unlike many other polymer forming or gelation systems, the compositions and methods disclosed herein do not require chemical or photoinitiators that may be cytotoxic. The crosslinking functional groups (boronic acid moieties and hydroxamic acid moieties) can provide rapid gelation (in the order of seconds to minutes), are stable under most pH conditions, and present a bioadhesive character. Furthermore, hydrogels formed as disclosed herein can have shear thinning and viscoelastic recovery properties, which are uncommon for crosslinked hydrogel networks and can enhance their efficacious use in injectable applications. As such, the disclosed polymeric compositions can be particularly useful in applications in which injection is followed by retention of material.

In some specific examples, the polymeric compositions disclosed herein can comprise one or more moieties having Formula I:

$$R^1—(Z)_n—R^2 \qquad (I)$$

where $R^1$ and $R^2$ are residues of a polymer, Z is a moiety formed from a reaction between a boronic acid moiety and a hydroxamic acid moiety ("the crosslinking moiety"), and n is at least 1. In other examples, n is 2, 3, 4, 5, 6, 7, 8, 9, 10, or greater than 10, where any of the stated values can form an upper and/or lower endpoint when appropriate.

$R^1$ and $R^2$ can be residues of the same polymer or residues of different polymers. Also, there can be other polymer residues in the disclosed compositions, e.g., residues $R^3$, $R^4$, $R^5$, $R''$, etc (where n is an integer). Such additional polymer residues can be linked to either or both residues $R^1$ and $R^2$. The additional polymer residues can be linked via crosslinking moiety Z as defined herein or through some other linking moiety.

Formula I represents one type of crosslinking structure that can be present in the disclosed polymeric compositions. In this crosslinking structure, Z represents a covalent crosslink (e.g., a boronate ester) between the polymer residues $R^1$ and $R^2$, which is formed from a reaction between a boronic acid moiety and a hydroxamic acid moiety. There can be one crosslinking moiety (Z) in the disclosed polymeric compositions, i.e., n is 1, or, more typically, more than one crosslinking moiety (Z), i.e., n is more than 1. The crosslinking structure illustrated by Formula I can be formed by the methods disclosed herein.

Generally, the polymer residues, $R^1$ and $R^2$, of the disclosed polymeric compositions are derived from a polymer, denoted $R^{1'}$ and $R^{2'}$, respectively. The polymer $R^{1'}$ comprises one or more boronic acid moieties, denoted X. The polymer $R^{2'}$ comprises one or more hydroxamic acid moieties, denoted Y. When polymer $R^{1'}$ with its one or more boronic acid moieties (denoted empirically as $R^{1'}$—X) and polymer $R^{2'}$ with its one or more hydroxamic acid moieties (denoted empirically as $R^{2'}$—Y) are reacted together, a boronic acid moiety and a hydroxamic acid moiety, X and Y, undergo a reaction with one another to produce the crosslinking moiety Z (e.g., a boronate ester) in Formula I above. Thus, Z links the remaining residue of one polymer, i.e., $R^1$, to the remaining residue of the other polymer, i.e., $R^2$. This general reaction scheme (Scheme 1) can be illustrated as follows:

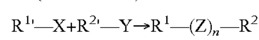

$$R^{1'}—X+R^{2'}—Y \rightarrow R^1—(Z)_n—R^2 \qquad \text{Scheme 1}$$

While the polymer $R^{1'}$ is shown with one X substituent (i.e., a boronic acid moiety) in Scheme 1, it is understood that more than one X substituent can, and often will, be present on $R^{1'}$. In this sense, $R^{1'}$ can be said to be multivalent. Similarly, while the polymer $R^{2'}$ is shown with one Y substituent (i.e., a hydroxamic acid moiety) in Scheme 1, it is understood that more than one Y substituent can, and often will, be present on $R^{2'}$. Again, in this sense, $R^{2'}$ can be said to be multivalent. Depending on the number of boronic acid moieties (X) and hydroxamic acid moieties (Y) present on each polymer $R^{1'}$ and $R^{2'}$, and the extent of the reaction between these moieties, the number of crosslinking moieties (Z) formed by such a reaction will vary. For example, if polymer $R^{1'}$ contains two boronic acid moieties (X), and polymer $R^{2'}$ contains two hydroxamic acid moieties (Y), and the reaction between the boronic acid and hydroxamic moieties proceeds to completion, then there will be two crosslinking moieties (Z) (i.e., n will be 2 in Formula I). It is contemplated, however, that at least one reaction between a boronic acid moiety (X) and a hydroxamic acid moiety (Y) will occur, thus providing at least one crosslinking moiety (Z) between the two remaining polymer residues $R^1$ and $R^2$.

Further, Scheme 1 is empirical only and is not meant to imply a 1 to 1 stoichiometric relationship between the polymer residues $R^1$ and $R^2$. More than one polymer $R^{1'}$ can react with polymer $R^{2'}$ and vice versa. It is contemplated that the ratio of polymer residues $R^1$ and $R^2$ can vary, as can the number of boronic acid and/or hydroxamic acid moieties on these polymers. The ratio of polymers and the amount of crosslinking can vary depending on the desires of the practitioner. For example, the ratio of polymer residues $R^1$ and $R^2$ can be about 1:70, 5:70, 10:70, 15:70, 20:70, 25:70, 30:70, 70:30, 70:25, 70:20, 70:15, 70:10, 70:5, 70:1, 1:65, 5:65, 10:65, 15:65, 20:65, 25:65, 30:65, 35:65, 65:35, 65:30, 65:25, 65:20, 65:15, 65:10, 65:5, 65:1, 1:60, 5:60, 10:60, 15:60, 20:60, 25:60, 30:60, 35:60, 40:60, 60:40, 60:35, 60:30, 60:25, 60:20, 60:15, 60:10, 60:5, 60:1, 1:55, 5:55, 10:55, 15:55, 20:55, 25:55, 30:55, 35:55, 40:55, 45:55, 55:45, 55:40, 55:35, 55:30, 55:25, 55:20, 55:15, 55:10, 55:5, 55:1, 1:50, 5:50, 10:50, 15:50, 20:50, 25:50, 30:50, 35:50, 40:50, 45:50, 50:50, 50:45, 50:40, 50:35, 50:30, 50:25, 50:20, 50:15, 50:10, 50:5, 50:1, 1:45, 5:45, 10:45, 15:45, 20:45, 25:45, 30:45, 35:45, 40:45, 45:45, 45:40, 45:35, 45:30, 45:25, 45:20, 45:15, 45:10, 45:5, 45:1, 1:40, 5:40, 10:40, 15:40, 20:40, 25:40, 30:40, 35:40, 40:40, 40:35, 40:30, 40:25, 40:20, 40:15, 40:10, 40:5, 40:1, 1:35, 5:35, 10:35, 15:35, 20:35, 25:35, 30:35, 35:35, 35:30, 35:25, 35:20, 35:15, 35:10, 35:5, 35:1, 1:30, 5:30, 10:30, 15:30, 20:30, 25:30, 30:30, 30:25, 30:20, 30:15, 30:10, 30:5, 30:1, 1:25, 5:25, 10:25, 15:25, 20:25, 25:25, 25:20, 25:15, 25:10, 25:5, 25:1, 1:20, 5:20, 10:20, 15:20, 20:20, 20:15, 20:10, 20:5, 20:1, 1:15, 5:15, 10:15, 15:15, 15:10, 15:5, 15:1, 1:10, 5:10, 10:10, 10:5, 10:1, 1:5, 5:5, or 5:1. In one particular example, the ratio of $R^1$ to $R^2$ is about 1:1.

A further schematic of a polymer composition as described by Formula I and Scheme 1 is shown in FIG. 1. Here, a polymer containing phenylboronic acid moieties is reacted with a polymer containing salicylhydroxamic moieties to provide a crosslinked polymer matrix or network. Two possible crosslinking moieties produced from this reaction, which would correspond to Z in Formula I and Scheme 1, are shown in the expanded view of FIG. 1.

In another variation of the polymer compositions disclosed herein, the polymers $R^{1'}$ and $R^{2'}$ need not contain a single type of reactive moiety. That is, $R^{1'}$ need not contain boronic acid (X) as the sole type of reactive moiety. For example, polymer $R^{1'}$ can contain boronic acid (X) and hydroxamic acid (Y) moieties. Likewise, polymer $R^{2'}$ can contain boronic acid (X) and hydroxamic acid (Y) moieties. In such a situation, a boronic acid moiety on a polymer can react with a hydroxamic acid moiety on the same polymer or on a different polymer to yield a crosslinking moiety (Z). One way of illustrating this is shown in Scheme 2.

Scheme 2

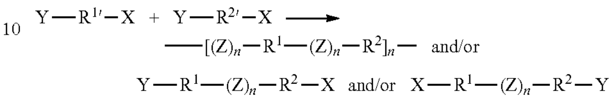

$$Y—R^{1'}—X + Y—R^{2'}—X \longrightarrow —[(Z)_n—R^1—(Z)_n—R^2]_n— \text{ and/or } Y—R^1—(Z)_n—R^2—X \text{ and/or } X—R^1—(Z)_n—R^2—Y$$

While the polymer $R^{1'}$ is shown with one X and one Y substituent in Scheme 2, it is understood that more than one X and/or more than one Y can be present on $R^{1'}$. Similarly, while the polymer $R^{2'}$ is shown with one Y and one X substituent in Scheme 2, it is understood that more than one Y and/or more than one X can be present on $R^{2'}$.

It is contemplated that all of the possible products shown in Scheme 2 are intended to be within the definition of Formula I; that is, the products shown in Scheme 2 all comprise the moiety $R^1—(Z)_n—R^2$. Further, in some other examples of the disclosed polymeric compositions, there can be one moiety having Formula I. In this situation, the polymeric composition can be said to have one crosslinking structure whereby one polymer residue, $R^1$, is linked to another polymer residue, $R^2$, with a crosslinking moiety, Z, formed by a reaction between a boronic acid moiety and a hydroxamic acid moiety. However, there are typically multiple crosslinking structures represented by Formula I in the disclosed polymeric compositions. Such compositions can be a network of multiple polymer residues, $R^1$ and $R^2$, linked together with multiple crosslinking moieties Z formed from the reaction between multiple boronic acid moieties and multiple hydroxamic acid moieties. One such polymeric composition is shown in FIG. 1. Also, such polymeric compositions can comprise a hydrogel, such as when one or more of the polymer residues is a hydrophilic polymer residue. It is also contemplated that other types of crosslinking structures can be present in the disclosed polymeric compositions.

In a further example of a crosslinking structure that can be present in the disclosed polymeric compositions, the disclosed polymeric composition can comprise one or more moieties having Formula II:

$$L\text{-}(Z—R^1)_m \quad (II)$$

where L is a residue of a linker agent, $R^1$ and Z are as defined above, and m is at least 2. In other examples, m is 2, 3, 4, 5, 6, 7, 8, 9, 10, or greater than 10, where any of the stated values can form an upper and/or lower endpoint when appropriate.

In Formula II, Z represents a link between a linker residue, L, and a polymer residue, $R^1$. The crosslinked structure illustrated by Formula II can also be formed by the methods disclosed herein.

As discussed above, the polymer residue, $R^1$, is derived from a polymer, denoted $R^{1'}$. The polymer $R^{1'}$ can comprise one or more boronic acid moieties, denoted X. The linker residue, L, is derived from a linker agent, denoted L', which can comprise two or more hydroxamic acid moieties. When the polymer, with its one or more boronic acid moieties (denoted empirically as $R^{1'}—X$), and the linker agent, with its two or more hydroxamic acid moieties (denoted empirically as $L'\text{-}Y_m$), are reacted together, the moieties X and Y undergo a reaction to produce the crosslinking moiety Z in Formula II above. Alternatively, the polymer, $R^{1'}$, can comprise one or more hydroxamic acid moieties, denoted Y, and the linker agent, L', can comprise two or more boronic acid moieties, denoted X. When the polymer, with its one or more hydroxamic acid moieties (denoted empirically as $R^1$—Y), and the linker agent, with its two or more boronic acid moieties (denoted empirically as $L'\text{-}X_m$), are reacted together, the moieties X and Y undergo a reaction to produce the crosslinking moiety Z in Formula II above. Thus, in both of these alternatives, Z links the remaining residue of the polymer, i.e., $R^1$, to the remaining residue of the linker agent, i.e., L. The general reaction schemes (Scheme 3) can be illustrated as follows:

Scheme 3

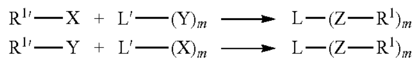

$$R^{1\prime}—X + L'—(Y)_m \longrightarrow L—(Z—R^1)_m$$
$$R^{1\prime}—Y + L'—(X)_m \longrightarrow L—(Z—R^1)_m$$

While the polymer $R^{1\prime}$ is shown with either one X substituent or one Y substituent in Scheme 3, it is understood that more than one X or more than one Y can, and often will, be present on $R^{1\prime}$. It is also possible for the polymer, $R^{1\prime}$, to comprise one or more boronic acid moieties (X) and one or more hydroxamic acid moieties (Y). Further Scheme 3, like the other schemes shown herein, is empirical only and is not meant to imply a 1 to 1 stoichiometric relationship between the linker residue, the polymer, and/or the reactive moieties. More than one polymer ($R^{1\prime}$—X and/or $R^{1\prime}$—Y) can react with more than one linker agent (L'-X and/or L'-Y). Also, more than one linker agent can react with the same polymer. Alternatively, more than one polymer can react with the same linker agent.

In the disclosed polymeric compositions, if L is a residue of divalent linker agent (e.g., the linker agent L' contained two hydroxamic moieties, Y, that each formed bonds with a boronic acid moiety, X, on the same or different polymer, $R^{1\prime}$), then m will be 2. Similarly, if L is a residue of trivalent linker agent, then m will be 3, and so forth. In certain examples, disclosed herein are polymeric compositions where linker residue, L, is a residue of a di-, tri-, tetra-, penta-, hexa-, hepta-, octa-, nona-, or deca-valent linker agent. In reference to Formula II, disclosed herein are polymeric compositions where m is 2, 3, 4, 5, 6, 7, 8, 9, 10, or greater than 10.

Further examples of this include polymeric compositions prepared from a divalent linker agent L' that comprises two boronic acid moieties, which each react with a hydroxamic acid moiety, Y, on the same or different polymer $R^{1\prime}$. Again, in this situation m will be 2. The divalent linker can comprise a boronic acid and hydroxamic acid moiety, which can respectively react with a hydroxamic acid and boronic acid moiety on the same or different polymer.

In some examples of the disclosed polymeric compositions, there can be one moiety having Formula II. In this situation, the polymeric composition can be said to have one crosslinking structure whereby a linker residue, L, is linked to a polymer residue, $R^1$, with a crosslinking moiety, Z, formed by a reaction between a boronic acid moiety and a hydroxamic acid moiety. However, as described above, there are typically multiple crosslinking structures represented by Formula II in the disclosed polymeric compositions. The disclosed composition can also have crosslinking structures represented by both Formula I and II. Such compositions can be a network of multiple polymer residues linked via crosslinking moieties derived from reactions between boronic acid moieties and hydroxamic acid moieties. Such polymeric compositions can comprise a hydrogel. It is also contemplated that other types of crosslinking structures can be present in the disclosed polymeric compositions.

The polymeric compositions described herein can assume numerous shapes and forms depending upon the intended end-use. In one example, the composition is or can be formed into a laminate, a gel, a bead, a sponge, a film, a mesh, a matrix, a particle, filament, or nanoparticle. The procedures disclosed in U.S. Pat. Nos. 6,534,591 and 6,548,081, which are incorporated by reference in their entireties, can be used for preparing polymeric compositions having different forms.

The polymeric compositions disclosed herein can also be biodegradable. For example, the disclosed polymeric compositions can be biodegradable by peptides such as naturally occurring enzymes that can degrade the polymeric compositions over time. In other examples, the biodegradable polymeric compositions can be a peptide, orthoester, alpha-hydroxy ester, phosphazene, or polymer thereof.

Polymers and Residue Thereof

The polymers, $R^{1\prime}$, $R^{2\prime}$, $R^{3\prime}$, $R^{n\prime}$, etc., and likewise the residues derived therefrom, $R^1$, $R^2$, $R^3$, $R^n$, etc., can be any polymeric compound. The molecular weight of the polymer or residue thereof can vary and will depend upon the selection of the polymer(s) and/or the linker agent and the particular application (e.g., whether a hydrogel is to be prepared and its intended use). In one example, the polymer can have a molecular weight of from about 2,000 Da to about 2,000,000 Da. In another aspect, the molecular weight of the polymer can be about 5,000; 10,000; 20,000; 30,000; 40,000; 50,000; 75,000; 100,000; 200,000; 250,000; 300,000; 350,000; 400,000; 450,000; 500,000; 550,000; 600,000; 650,000; 700,000; 750,000; 800,000; 850,000; 900,000; 950,000; 1,000,000; 1,500,000; or 2,000,000 Da, where any stated values can form a lower and/or upper endpoint of a molecular weight range as appropriate.

All or a portion of a polymeric compound suitable for use herein can be hydrophilic or hydrophobic. By "hydrophilic" is meant that the polymer or residue thereof is soluble at or greater than about 1 mg/L of water. By "hydrophobic" is meant that the polymer or residue thereof is soluble at less than about 1 mg/L of water. For example, a hydrophilic polymer or residue thereof can be soluble at about 5 mg/L, 10 mg/L, 50 mg/L, 100 mg/L, 500 mg/L, or greater than 1 g/L. In another example, a hydrophobic polymer or residue thereof can be soluble at about less than about 1 g/L, less than about 0.5 g/L, less than about 0.1 g/L, less than about 0.05 g/L, or less than about 0.01 g/L, or insoluble in water.

For example, a hydrophilic polymer or residue thereof can comprise a homopolymer or a copolymer (e.g., a block, graft, or graft comb copolymer) where one or more of the polymer blocks comprise a hydrophilic segment. In another example, a hydrophobic polymer or residue thereof can comprise a homopolymer or a copolymer (e.g., a block, graft, or graft comb copolymer) where one or more of the polymer blocks comprise a hydrophobic segment. Suitable hydrophilic and hydrophobic polymers and residues thereof can be obtained from commercial sources or can be prepared by methods known in the art.

Many suitable hydrophilic polymers and residues thereof can form hydrogels. Suitable hydrophilic polymers and residues thereof can include any number of polymers based on diol- or glycol-containing linkages, for example, polymers comprising polyethylene glycol (PEG), also known as polyethylene oxide (PEO), and polypropylene oxide (PPO). Other suitable examples include polymers comprising multiple segments or blocks of PEG alternating with blocks of polyester, for example, POLYACTIVE™ is a copolymer that has large blocks of PEG alternating with blocks of poly(butylene terephthalate). Still other suitable examples include hydrophilic-substituted poly(meth)acrylates, polyacrylates, poly(meth)acrylamides and polyacrylamides, such as poly(hydroxypropyl)methacrylamide.

Another example of suitable polymers are those that contain a residue of a sulphonamide or sulphonamide derivative.

Suitable hydrophobic polymers and residues thereof can include any number of polymers based on olefin, ester, or amide polymerizations. For example, suitable hydrophobic polymers include polyethylene, polypropylene, polybutylene, poly(meth)acrylates, polystyrene, polyamide (e.g., nylon and polycaprolactam), polyacrylonitrile, polyesters, polyurethanes, and the like.

Further examples of hydrophobic polymers are siloxanes, such as decamethylcyclopentasiloxane, octamethylcyclotetrasiloxane, cyclomethicone, dimethicone and mixtures thereof.

In one example, a polymer or residue thereof can comprise a multi-branched polymer (e.g., multi-armed PEG). Multi-branched polymers are polymers that have various polymeric chains (termed "arms" or "branches") that radiate out from a central core. For example, a suitable hydrophilic polymer or residue thereof can comprise a 2, 3, 4, 5, 6, 7, 8, 9, or 10 armed-PEGs. Such multi-arm polymers are commercially available or can be synthesized by methods known in the art.

Many suitable multi-armed polymers are referred to as dendrimers. The term "dendrimer" means a branched polymer that possesses multiple generations, where each generation creates multiple branch points. "Dendrimers" can include dendrimers having defects in the branching structure, dendrimers having an incomplete degree of branching, crosslinked and uncrosslinked dendrimers, asymmetrically branched dendrimers, star polymers, highly branched polymers, highly branched copolymers and/or block copolymers of highly branched and not highly branched polymers.

Any dendrimer can be used in the disclosed compositions and methods. Suitable examples of dendrimers that can be used include, but are not limited to, poly(propyleneimine) (DAB) dendrimers, benzyl ether dendrimers, phenylacetylene dendrimers, carbosilane dendrimers, convergent dendrimers, polyamine, and polyamide dendrimers. Other useful dendrimers include, for example, those described in U.S. Pat. Nos. 4,507,466, 4,558,120, 4,568,737 and 4,587,329, as well as those described in Dendritic Molecules, Concepts, Syntheses, Perspectives. Newkome, et al., VCH Publishers, Inc. New York, N.Y. (1996), which are incorporated by reference herein for at least their teachings of dendrimers.

In one example, a suitable polymer or residue thereof comprises a triblock polymer of poly(ethylene oxide)-poly(propylene oxide)-poly(ethylene oxide). These polymers are referred to as PLUORONICS™. PLUORONICS™ are commercially available from BASF (Florham Park, N.J.) and have been used in numerous applications as emulsifiers and surfactants in foods, as well as gels and blockers of protein adsorption to hydrophobic surfaces in medical devices. These materials have low acute oral and dermal toxicity, and do not cause irritation to eyes or inflammation of internal tissues in man. The hydrophobic PPO block adsorbs to hydrophobic (e.g., polystyrene) surfaces, while the PEO blocks provide a hydrophilic coating that is protein-repellent. PLUORONICS™ have low toxicity and are approved by the FDA for direct use in medical applications and as food additives. Surface treatments with PLUORONICS™ can also reduce platelet adhesion, protein adsorption, and bacterial adhesion.

In another example, a suitable polymer or residue thereof can comprise a triblock polymer of poly(ethylene oxide)-poly(propylene oxide)-poly(ethylene oxide), wherein the polymer has a molecular weight of from 1,000 Da to 100,000 Da. In still another example, a suitable polymer or residue thereof is a triblock polymer of poly(ethylene oxide)-poly(propylene oxide)-poly(ethylene oxide), wherein the polymer has a molecular weight of from having a lower endpoint of 1,000 Da, 2,000 Da, 3,000 Da, 5,000 Da, 10,000 Da, 15,000 Da, 20,000 Da, 30,000 and an upper endpoint of 5,000 Da, 10,000 Da, 15,000 Da, 20,000 Da, 25,000 Da, 30,000 Da, 40,000 Da, 50,000 Da, 60,000 Da, 70,000 Da, 80,000 Da, 90,000 Da, or 100,000 Da, wherein any lower endpoint can be matched with any upper endpoint, wherein the lower endpoint is less than the upper endpoint. In a further example, a suitable polymer or residue thereof can comprise a triblock polymer of poly(ethylene oxide)-poly(propylene oxide)-poly(ethylene oxide), wherein the polymer has a molecular weight of from 5,000 Da to 15,000 Da. In yet a further example, the triblock polymer of poly(ethylene oxide)-poly(propylene oxide)-poly(ethylene oxide) is PEO103-PPO39-PEO103, PEO132-PPO50-PEO132, or PEO100-PPO65-PEO100. In yet another example, the polymer is PEO103-PPO39-PEO103, PEO132-PPO50-PEO132, or PEO100-PPO65-PEO100.

Additional polymers and residues thereof can be those based on acrylic acid derivatives, such homopolymers or copolymers of as poly(meth)acrylate, polyvinyl alcohol, polyacrylonitrile, polyacrylamides, poly(alkylcyanoacrylates), and the like. Still other examples include polymers based on organic acids such as, but not limited to, polyglucuronic acid, polyaspartic acid, polytartaric acid, polyglutamic acid, polyfumaric acid, polylactide, and polyglycolide, including copolymers thereof. For example, polymers can be made from lactide and/or glycolide monomer units along with a polyether hydrophilic core segment as a single block in the backbone of the polymer. Suitable polymers that are based on esters include, but are not limited to, poly(ortho esters), poly(block-ether esters), poly(ester amides), poly(ester urethanes), polyphosphonate esters, polyphosphoesters, polyanhydrides, and polyphosphazenes, including copolymers thereof.

Still further examples of suitable polymers and residues thereof include, but are not limited to, polyhydroxyalkanoates, poly(propylene fumarate), polyvinylpyrrolidone, polyvinyl polypyrrolidone, polyvinyl-N-methylpyrrolidone, hydroxypropylcellulose, methylcellulose, sodium alginate, gelatin, acid-hydrolytically-degraded gelatin, agarose, carboxymethylcellulose, carboxypolymethylene, poly(hydroxypropyl methacrylate), poly(hydroxyethyl methacrylate), and poly(2-hydroxypropyl methacrylamide).

Particularly suitable polymers or residues thereof are those that form hydrogels. Examples of hydrogels useful herein include, but are not limited to, aminodextran, dextran, DEAE-dextran, chondroitin sulfate, dermatan, heparan, heparin, chitosan, polyethyleneimine, polylysine, dermatan sulfate, heparan sulfate, alginic acid, pectin, carboxymethylcellulose, hyaluronic acid, agarose, carrageenan, starch, polyvinyl alcohol, cellulose, polyacrylic acid, polyacrylamide, polyethylene glycol, or the salt or ester thereof, or a mixture thereof. In one example, the hydrogel can comprise carboxymethyl dextran having a molecular weight of from 5,000 Da to 100,000 Da, 5,000 Da to 90,000 Da; 10,000 Da to 90,000 Da; 20,000 Da to 90,000 Da; 30,000 Da to 90,000 Da; 40,000 Da to 90,000 Da; 50,000 Da to 90,000 Da; or 60,000 Da to 90,000 Da. Still other examples of hydrogels include, but are not limited to, poly(N-isopropyl acrylamide), poly(hydroxy ethylmethacrylate), poly(vinyl alcohol), poly(acrylic acid), polyethylene glycol diacrylate, polyethylene glycol dimethacrylate, and combinations thereof.

In further examples, a suitable polymer or residue thereof can be a polysaccharide. Any polysaccharide known in the art can be used herein. Examples of polysaccharides include starch, cellulose, glycogen or carboxylated polysaccharides such as alginic acid, pectin, carboxymethyl amylose, or carboxymethylcellulose. Further, any of the polyanionic polysaccharides disclosed in U.S. Pat. No. 6,521,223, which is incorporated by reference in its entirety, can be used as a suitable polymer or residue thereof. In one example, the polysaccharide can be a glycosaminoglycan (GAG). A GAG is one molecule with many alternating subunits. For example, hyaluronan is $(GlcNAc\text{-}GlcUA\text{-})_x$. Other GAGs are sulfated at different sugars. Generically, GAGs are represented by Formula III: A-B-A-B-A-B, where A is an uronic acid and B is an aminosugar that is either O- or N-sulfated, where the A and B units can be heterogeneous with respect to epimeric content or sulfation.

There are many different types of GAGs, having commonly understood structures, which, for example, are within the disclosed compositions, such as chondroitin, chondroitin sulfate, dermatan, dermatan sulfate, heparin, or heparan sulfate. Any GAG known in the art can be used in any of the methods described herein. Glycosaminoglycans can be purchased from Sigma, and many other biochemical suppliers. Alginic acid, pectin, and carboxymethylcellulose are among other carboxylic acid containing polysaccharides useful in the methods described herein.

In one example, the polysaccharide is hyaluronan (HA). HA is a non-sulfated GAG. Hyaluronan is a well known, naturally occurring, water soluble polysaccharide composed of two alternatively linked sugars, D-glucuronic acid and N-acetylglucosamine. The polymer is hydrophilic and highly viscous in aqueous solution at relatively low solute concentrations. It often occurs naturally as the sodium salt, sodium hyaluronate. Other salts such as potassium hyaluronate, magnesium hyaluronate, and calcium hyaluronate, are also suitable. Methods of preparing commercially available hyaluronan and salts thereof are well known. Hyaluronan can be purchased from Seikagaku Company, Clear Solutions Biotech, Inc., Pharmacia Inc., Sigma Inc., and many other suppliers. For high molecular weight hyaluronan it is often in the range of about 100 to about 10,000 disaccharide units. In another aspect, the lower limit of the molecular weight of the hyaluronan is from about 1,000 Da, 2,000 Da, 3,000 Da, 4,000 Da, 5,000 Da, 6,000 Da, 7,000 Da, 8,000 Da, 9,000 Da, 10,000 Da, 20,000 Da, 30,000 Da, 40,000 Da, 50,000 Da, 60,000 Da, 70,000 Da, 80,000 Da, 90,000 Da, or 100,000 Da, and the upper limit is 200,000 Da, 300,000 Da, 400,000 Da, 500,000 Da, 600,000 Da, 700,000 Da, 800,000 Da, 900,000 Da, 1,000,000 Da, 2,000,000 Da, 4,000,000 Da, 6,000,000 Da, 8,000,000 Da, or 10,000,000 Da, where any of the lower limits can be combined with any of the upper limits.

It is also contemplated that a suitable polymer can have hydrolysable or biochemically cleavable groups incorporated into the polymer network structure. Examples of such hydrogels are described in U.S. Pat. Nos. 5,626,863, 5,844,016, 6,051,248, 6,153,211, 6,201,065, 6,201,072, all of which are incorporated herein by reference in their entireties.

In other examples, the polymer or residues thereof can contain moieties that can modify (i.e., increase, decrease, make reversible or irreversible, or stabilize) the binding affinity of the crosslinking moieties. For example, charged polymers can affect the pH at which the crosslinking moieties react to form a crosslink. Examples of suitable polymers or residues thereof that can be used in whole or in part in the disclosed polymeric compositions to modify the binding affinity of the crosslinking moieties are polymers that have negatively charged residues or moieties, or residues or moieties that can be made negative, such as polyacids, e.g., polyacrylic acid, polymethacrylic acid, and others disclosed herein, polysulfonates, and polyols, or polymers that have positively charged residues or moieties or residues or moieties that can be made positive such as polyamines.

As noted previously, the disclosed polymers, $R^{1\prime}$, $R^{2\prime}$, $R^{3\prime}$, $R^{n\prime}$, etc., can contain at least one boronic acid moiety, X, and/or at least one hydroxamic acid moiety, Y, as are described herein. In other examples, the polymer(s) can comprise 1, 2, 3, 4, 5, 6, 7, 8, 9, 10, or more boronic acid and/or hydroxamic acid moieties. In still other examples, the polymer(s) can comprise greater than or equal to 10, 15, or 20 boronic acid and/or hydroxamic acid moieties. When the disclosed polymer(s) comprises more than one boronic acid and/or hydroxamic acid moieties, the reactive moieties can be the same or different. The number of boronic acid and/or hydroxamic acid moieties present on the disclosed polymer(s) can vary depending upon the amount and type of polymer, the type of linker agent, the amount and type of boronic acid and/or hydroxamic acid moieties, preference, and the like.

The boronic acid and/or hydroxamic acid moieties can be produced in various ways depending on the particular polymer and the particular boronic acid and/or hydroxamic acid moiety. For example, a monomer containing a particular boronic acid and/or hydroxamic acid moiety can be polymerized together to form a polymer or a segment of a suitable polymer. Also, a functional group on a suitable polymer can be converted chemically to a boronic acid and/or hydroxamic acid reactive moiety. For example, cyclo(ethylene)ester boronates can be hydrolyzed to boronic acid, and benzenecarbomethylester can be hydroxaminated to benzocarbohydroxamic acid. Alternatively, the boronic acid moiety can be produced by lithiation of a suitable aryl halide followed by reaction with a protected boron hydride or di boronate. This can then be in the polymer system.

Linker Agent and Residue Thereof

The linker agent, L′, can be any compound that contains at least two boronic acid moieties, at least two hydroxamic acid moieties, or at least one boronic acid moiety and at least one hydroxamic acid moiety, as are described herein. For example, the linker agent can comprise 2, 3, 4, 5, 6, 7, 8, 9, 10, or more such moieties. In other examples, the linker agent or residue thereof can comprise greater than or equal to 10, 15, or 20 boronic acid and/or hydroxamic acid moieties. The boronic acid and/or hydroxamic acid moieties can be the same or different. The number of boronic acid and/or hydroxamic acid moieties present on the linker agent can vary depending upon the amount and type of polymer(s), the type of linker agent, the type of boronic acid and/or hydroxamic acid moieties, preference, and the like.

The linker agent or residue thereof need not be hydrophilic or hydrophobic, although in many cases it can be hydrophilic and contain one or more hydrophilic segments. When the linker agent comprises a hydrophilic polymer or segment thereof, any of the hydrophilic polymers and segments thereof disclosed herein can be used. Likewise, when the linker agent comprises a hydrophobic polymer or segment thereof, any of the hydrophobic polymers and segments thereof disclosed herein can be used.

In some example, the linker agent or residue thereof can comprise a $C_1$-$C_6$ branched or straight-chain alkyl, such as methyl, ethyl, n-propyl, isopropyl, n-butyl, isobutyl, sec-butyl, tert-butyl, n-pentyl, isopentyl, neopentyl, sec-pentyl, or hexyl. In a specific example, the linker agent or residue thereof can comprise a polyalkylene (i.e., $—(CH_2)_n—$, wherein n is from 1 to 5, from 1 to 4, from 1 to 3, or from 1 to 2). In another example, the linker agent or residue thereof can comprise a $C_1$-$C_6$ branched or straight-chain alkoxy such as a methoxy, ethoxy, n-propoxy, isopropoxy, n-butoxy, isobutoxy, sec-butoxy, tert-butoxy, n-pentoxy, isopentoxy, neopentoxy, sec-pentoxy, or hexoxy.

In still other examples, the linker agent or residue thereof can comprise a $C_2$-$C_6$ branched or straight-chain alkyl, wherein one or more of the carbon atoms are substituted with oxygen (e.g., an ether) or an amino group. For example, a suitable linker agent or residue thereof can include, but is not limited to, a methoxymethyl, methoxyethyl, methoxypropyl, methoxybutyl, ethoxymethyl, ethoxyethyl, ethoxypropyl, propoxymethyl, propoxyethyl, methylaminomethyl, methylaminoethyl, methylaminopropyl, methylaminobutyl, ethylaminomethyl, ethylaminoethyl, ethylaminopropyl, propylaminomethyl, propylaminoethyl, methoxymethoxymethyl, ethoxymethoxymethyl, methoxyethoxymethyl, methoxymethoxyethyl, and the like, and derivatives thereof. In one specific example, the linker agent or residue thereof can comprise a methoxymethyl (i.e., $CH_2$—O—$CH_2$—). In another specific example, the linker agent or residue thereof can comprise a polyether (e.g., —$(OCH_2CH_2)_m$, wherein m is an integer from 2 to 10 (i.e., 2, 3, 4, 5, 6, 7, 8, 9, or 10).

The reaction between the linker agent and the polymer results in a chemical bond that links the linker agent to the hydrophilic polymer, i.e., Z in Formula II. As noted herein, such reactions can occur as a result of a boronic acid moiety reacting with a hydroxamic acid moiety to form a boronate ester moiety, which are present on the polymer(s) and linker agent.

Reactive Moieties

The polymer(s) and linker agents disclosed herein can contain boronic acid and/or hydroxamic acid moieties. It is not critical that a particular reactive moiety be present on a particular polymer or linker agent so long as a crosslinking moiety (i.e., Z) is formed by the reaction of a boronic acid moiety with a hydroxamic acid moiety. Thus, at least one polymer can have at least one boronic acid moiety and at least one other polymer can have at least one hydroxamic moiety. Also, at least one polymer can have at least one boronic acid moiety and at least one other polymer can have both at least one boronic acid and at least one hydroxamic acid moieties. Still further, at least one polymer can have at least one hydroxamic acid moiety and at least one other polymer can have both at least one boronic acid and at least one hydroxamic acid moieties. In yet a further example, at least two polymers can have both at least one boronic acid and at least one hydroxamic acid moieties. In another example, at least one polymer can have at least one boronic acid moiety and at least one linker agent can have at least one hydroxamic moiety. Alternatively, at least one polymer can have at least one hydroxamic acid moiety and at least one linker agent can have at least one boronic acid moiety. Still further, at least one polymer can have at least one boronic acid moiety and at least one linker agent can have both at least one boronic acid and at least one hydroxamic acid moieties. Still further, at least one polymer can have at least one hydroxamic acid moiety and at least linker agent can have both at least one boronic acid and at least one hydroxamic acid moieties. In yet a further example, at least one polymer can have both at least one boronic acid and at least one hydroxamic acid moieties and at least one linker agent can have both at least one boronic acid and at least one hydroxamic acid moieties.

In the formulas below, the reactive moieties can be connected to the polymer(s) or linker agent by any type of bond or linkage, which can be of any length or size. For example, the reactive moiety can be connected directly to the polymer or linker agent, or connected via an alkyl, polyether, polyamide, or aryl group. These and other suitable connections are generically shown in the formulas below by the symbol:

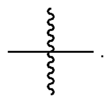

Boronic Acid Moiety

A boronic acid moiety is any chemical compound or fragment thereof that contains a —$B(OH)_2$ group. The boronic acid moiety and the hydroxamic acid moiety disclosed herein react with each other to form a covalent link, Z, between the remaining residues of the polymer(s) or between the remaining residues of the polymer(s) and the linker agent. The type of boronic acid moieties used will depend on the particular polymers, linker agent, use, preference, and the like.

Boronic acids are typically derived synthetically from primary sources of boron, such as boric acid. Dehydration of boric acid with alcohols gives rises to borate esters, which are precursors of boronic acids. The secondary oxidation of boranes is also used to prepare boronic acids. Boronic acids can be desirable for the disclosed compositions and methods because of their low toxicity. They also degrade to environmentally friendly boric acid. A discussion of the various methods of preparation and properties of many boronic acid moieties can be found in "Boronic Acids." Dennis Hall, Ed., Wiley-VCH Verlag, 2005, which is incorporated by reference herein at least for its teachings of boronic acid derivatives, their preparation, and reactions that involve boronic acids.

In some specific examples, the boronic acid moiety can be an alkylboronic acid moiety, where a substituted or unsubstituted, branched or unbranched, alkyl group is substituted with one or more —$B(OH)_2$ substituents. In some specific examples, the alkylboronic acid moiety can have Formula IV.

Formula IV

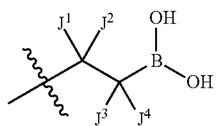

where $J^{1-4}$ are independently selected from the group consisting of hydrogen, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol substituents. In particular examples of alkylboronic acids, substituents $J^1$ and $J^2$ can both be hydrogen and one of substituents $J^3$ and $J^4$ can be hydrogen and the other can be a hydroxy, an alkoxy (e.g., methoxy, ethoxy), a nitro, an amino, or a halide substituent. In yet another example of alkylboronic acids, substituents $J^3$ and $J^4$ can both be hydrogen and one of substituents $J^1$ and $J^2$ can be hydrogen and the other can be a hydroxy, an alkoxy (e.g., methoxy, ethoxy), a nitro, an amino, or a halide substituent. In another example, the alkylboronic acid moiety is a cyclic alkyl moiety (e.g., cyclohexyl) substituted with one or more —$B(OH)_2$ substituents.

In other examples, the boronic acid moiety can be an arylboronic acid moiety. An arylboronic acid contains an aryl group, including heteroaryl groups, as disclosed herein, substituted with one or more —$B(OH)_2$ substituents. In a specific example, the disclosed arylboronic acid moiety can be a phenylboronic acid as shown in Formula V.

Formula V

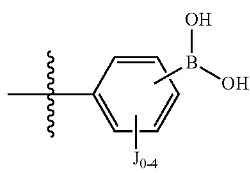

where 0 to 4 J substituents are present on the aryl ring and each J is independently selected from the group consisting of substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol. In particular examples of arylboronic acids generally and phenylboronic acids specifically, substituent J can be an ortho hydroxy, alkoxy (e.g., methoxy, ethoxy), nitro, amino, or halide substituent.

The boronic acid moiety can be attached to the polymer(s) (e.g., $R^{1'}$, $R^{2'}$, $R^{3'}$, $R^{m'}$, etc.) and/or the linker agent disclosed herein directly or by any suitable spacer moiety. Examples of spacer moieties include, but are not limited to, alkyl, polyethers, esters, diesters, amides, diamides, and the like. The spacer moiety can be about 1 to about 50 atoms in length (e.g., from 1 to about 25, from about 2 to about 18, from about 4 to about 12, from about 6 to about 10 atoms in length). One particularly suitable spacer moiety is an amide such as —$C(O)NH(CH_2)_p$ or a diamide such as —$C(O)NH(CH_2)_p$ NHC(O)—, where p is from 1 to 10 (e.g., 3).

In another example, the boronic acid moiety can comprise a bioactive agent.

Hydroxamic Acid Moiety

A hydroxamic acid moiety is any chemical compound or fragment thereof that contains a —C(O)NHOH group. The hydroxamic acid moiety and the boronic acid moiety disclosed herein react with each other to form a covalent link, Z, between the remaining residues of the polymer(s) or between the remaining residues of the polymer(s) and the linker agent. The type of hydroxamic acid moieties used will depend on the particular polymers, linker agent, use, preference, and the like.

Hydroxamic acid moieties can be prepared by methods known in the art. In one example, hydroxamic acid moieties can be prepared by coupling an activated carboxylic acid (e.g., methyl ester, cyano ester) with hydroxylamine under strong basic conditions (e.g., 1,8-diazobicyclo[5.4.0]undec-7-ene (DBU)). In another aspect, hydroxamic acid moieties can be prepared by coupling carboxylic acid with a protected hydroxylamine under suitable amino-acid coupling conditions. Protected hydroxylamines are commercially available or can be prepared by methods known in the art. Typically, protected hydroxylamines are prepared by reacting hydroxylamine with a suitable protecting group. The protecting groups that are used will depend on the specific reaction conditions, other substituents that may be present, availability, or preference. Conditions for coupling a protected hydroxylamine are well know in the art and typically involve contacting the carboxylic acid with the protected hydroxylamine in the presence of one or more activating agents. Various activating agents that can be used for the coupling reaction include, but are not limited to, 1-ethyl-3-(3-dimethylaminopropyl)carbodiimide (EDC), dicyclohexylcarbodiimide (DCC), N,N'-diisopropyl-carbodiimide (DIP), benzotriazol-1-yl-oxy-tris-(dimethylamino)phosphonium hexafluorophosphate (BOP), hydroxybenzotriazole (HOBt), and N-methylmorpholine (NMM), including a mixture thereof. The coupling reaction can be carried out in N-methylpyrrolidone (NMP) or in DMF. In one example, the coupling reaction can involve the treatment of the carboxylic acid with a protected hydroxylamine in the presence of EDC, HOBt, and NMM in DMF. See Tamura et al., *J Med Chem,* 41:640-649, 1998, which is incorporated by reference herein for its teaching of amine-acid coupling reactions. Removal of the protecting group can be done under hydrolytic conditions to result in a hydroxamic acid moiety.

In some specific examples, the hydroxamic acid moiety can be an alkylhydroxamic acid moiety, where a substituted or unsubstituted, branch or unbranched, alkyl group is substituted with one or more —C(O)NHOH substituents. In some specific examples, the alkylhydroxamic acid moiety can have Formula VI.

Formula VI

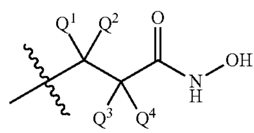

where $Q^{1-4}$ are independently selected from the group consisting of hydrogen, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol substituents. In particular examples of alkylhydroxamic acids, substituents $Q^1$ and $Q^2$ can both be hydrogen and one of substituents $Q^3$ and $Q^4$ can be hydrogen and the other can be a hydroxy, an alkoxy (e.g., methoxy, ethoxy), a nitro, an amino, or a halide substituent. In yet another example of alkylhydroxamic acids, substituents $Q^3$ and $Q^4$ can both be hydrogen and one of substituents $Q^1$ and $Q^2$ can be hydrogen and the other can be a hydroxy, an alkoxy (e.g., methoxy, ethoxy), a nitro, an amino, or a halide substituent. In another example, the alkylhydroxamic acid moiety is a cyclic alkyl (e.g., cyclohexyl) substituted with one or more —C(O)NHOH substituents.

In other examples, the hydroxamic acid moiety can be an arylhydroxamic acid moiety. An arylhydroxamic acid contains an aryl group, including heteroaryl groups, as disclosed herein, substituted with one or more —C(O)NHOH substituents. In a specific example, the disclosed arylhydroxamic acid moiety can be a phenylhydroxamic acid as shown in Formula VII.

Formula VII

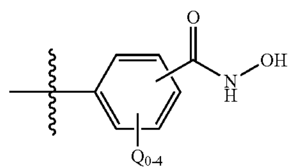

where 0 to 4 substituents Q are present on the aryl ring and each Q is independently selected from the group consisting of substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol.

The hydroxamic acid moiety can be attached to the polymer(s) (e.g., $R^{1\prime}$, $R^{2\prime}$, $R^{3\prime}$, $R^{\prime\prime\prime}$, etc.) and/or the linker agent directly or by any suitable spacer moiety. Examples of spacer moieties are as disclosed above and include, but are not limited to, alkyl, polyethers, esters, diesters, amides, diamides, and the like. The spacer moiety can be about 1 to about 50 atoms in length (e.g., from 1 to about 25, from about 2 to about 18, from about 4 to about 12, from about 6 to about 10 atoms in length). One particularly suitable spacer moiety for the hydroxamic acid moiety is an amide such as —C(O)NH$(CH_2)_p$ or a diamide such as —C(O)NH$(CH_2)_p$NHC(O)—, where p is from 1 to 10 (e.g., 3).

In some particular examples, the hydroxamic acid moiety can comprise a phenylhydroxamic acid with an ortho or meta substituent with at least one electron pair. Examples of such hydroxamic acid moieties are shown in Formula VIII.

Formula VIIIa

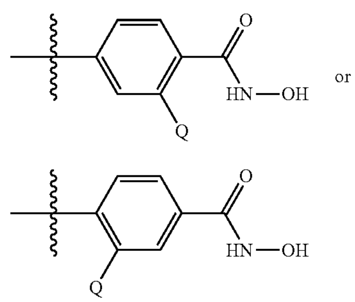

Formula VIIIb where Q is a hydroxy, amino, nitro, or alkoxy (e.g., methoxy, ethoxy) group. In one specific example, the hydroxamic acid moiety can comprise salicylhydroxamic acid.

In another example, the hydroxamic acid moiety can comprise a bioactive agent.

Specific Examples

In some specific examples of the polymer compositions disclosed herein, the polymer can be a multi-branched or graft polymer comprising one or more crosslinks formed from a reaction between one or more boronic acid and hydroxamic acid moieties. Multi-branched polymers, such as multi-arm PEG, include those polymers which have polymeric units comprising each arm. Graft polymers, such as poly(hydroxypropyl methacrylate), poly(hydroxyethyl methacrylate), and poly(hydroxypropyl methacrylamide), include those polymers which have polymeric units comprising either a linear chain or multiple branches as well as monomeric units comprising multiple branches.

In other examples of the disclosed polymer compositions, the polymer can be a multi-armed PEG polymer comprising one or more crosslinking reactive moieties as described herein. Specifically, the polymer can comprise a multi-arm PEG polymer comprising one or more boronic acid and/or hydroxamic acid. Also, the linker agent can be a multi-arm PEG polymer comprising one or more boronic acid and/or hydroxamic acid.

In other specific examples of the polymer compositions disclosed herein, the polymer(s) can be a graft copolymer or homopolymer, such as poly(hydroxypropyl methacrylate), poly(hydroxyethyl methacrylate), and poly(2-hydroxypropyl methacrylamide), on which grafts comprise one or more boronic acid and/or hydroxamic acid moieties. Specifically, the polymer(s) can comprise a graft copolymer or homopolymer, such as poly(hydroxypropyl methacrylate), poly(hydroxyethyl methacrylate), poly(2-hydroxypropyl methacrylamide), comprising one or more boronic acid and/or hydroxamic acid moieties. Also, the linker agent can be a graft copolymer or homopolymer, such as poly(hydroxypropyl methacrylate), poly(hydroxyethyl methacrylate), or poly (2-hydroxypropyl methacrylamide) comprising one or more boronic acid and/or hydroxamic acid moieties. Specific examples include polymers comprising one or more phenylboronic acid and polymers comprising one or more salicylhydroxamic acid, (2-hydroxyphenyl)-N-methoxycarboxamide, N-hydroxy-(2-hydroxyphenyl)-N-methylcarboxamide, and/or benzenecarbohydroxamic acid.

Pharmaceutically Acceptable Salts

Any of the polymeric compositions and components thereof described herein can be a pharmaceutically acceptable salt or ester thereof if they possess groups that are capable of being converted to a salt or ester. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like.

In some examples, if the polymeric composition or component thereof possesses a basic group, it can be protonated with an acid such as, for example, HCl or $H_2SO_4$, to produce the cationic salt. In one example, the compound can be protonated with tartaric acid or acetic acid to produce the tartarate or acetate salt, respectively. In another example, the reaction of the compound with the acid or base is conducted in water, alone or in combination with an inert, water-miscible organic solvent, at a temperature of from about 0° C. to about 100° C., such as at room temperature. In certain situations, where applicable, the molar ratio of the disclosed compounds to base is chosen to provide the ratio desired for any particular salts.

Ester derivatives are typically prepared as precursors to the acid form of the compounds and accordingly can serve as prodrugs. Generally, these derivatives will be lower alkyl esters such as methyl, ethyl, and the like.

Pharmaceutical Polymeric Compositions

In some examples, any of the compositions and components produced by the methods described herein can include at least one bioactive agent that is attached (either covalently or non-covalently) to the polymeric composition. The resulting pharmaceutical polymeric composition can provide a system for sustained, continuous delivery of drugs and other biologically-active agents to tissues adjacent to or distant from the application site. The bioactive agent is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include anti-viral agents, hormones, antibodies, or therapeutic proteins. Still other bioactive agents include prodrugs, which are agents that are not biologically active when administered but upon administration to a subject are converted to bioactive agents through metabolism or some other mechanism. Additionally, any of the compositions disclosed herein can contain combinations of two or more bioactive agents.

In some examples, the bioactive agents can include substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, 6α-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. All of these agents are commercially available from suppliers such as Sigma Chemical Co. (Milwaukee, Wis.).

Additionally, a substance or metabolic precursor which is capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-α (TGF-α), transforming growth factor-β (TGF-β), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like.

Other useful substances include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaprotemal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances. All of these agents are commercially available from suppliers such as Sigma Chemical Co. (Milwaukee, Wis.).

The pharmaceutical polymeric compositions can be prepared using techniques known in the art. In one aspect, the composition is prepared by admixing a polymeric composition disclosed herein with a bioactive agent. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having reactive carboxyl groups, can be undertaken on the compound. For example, first, carboxylate-containing chemicals such as anti-inflammatory drugs ibuprofen or hydrocortisone-hemisuccinate can be converted to the corresponding N-hydroxysuccinimide (NHS) active esters and can further react with an OH group of a polymer. Second, non-covalent entrapment of a bioactive agent in any of the disclosed compositions is also possible. Third, electrostatic or hydrophobic interactions can facilitate retention of a bioactive agent in the disclosed compositions. Fourth, a free hydroxamic acid or boronic acid moiety in the composition can respectively react with a boronic acid or hydroxamic acid moiety in a bioactive agent.

It will be appreciated that the actual preferred amounts of bioactive agent in a specified case will vary according to the specific compound being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators skilled in the art of determining doses of pharmaceutical compounds will have no problems determining dose according to standard recommendations (Physicians Desk Reference, Barnhart Publishing (1999)).

Pharmaceutical polymeric compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin, and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

The pharmaceutical polymeric composition can be administered in a number of ways depending on whether local or systemic treatment is desired, and on the area to be treated. Administration can be topically (including ophthalmically, vaginally, rectally, intranasally).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases, and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

In one aspect, any of the disclosed compositions can include living cells. Examples of living cells include, but are not limited to, fibroblasts, hepatocytes, chondrocytes, stem cells, bone marrow, muscle cells, cardiac myocytes, neuronal cells, or pancreatic islet cells.

Methods of Making

Disclosed herein are methods of making the disclosed polymeric compositions. These methods can also be used for crosslinking any of the components described herein to produce a polymeric composition. In one example, disclosed is a method of making a polymeric composition that comprises providing a first polymer comprising one or more hydroxamic acid moieties; providing a second polymer comprising one or more boronic acid moieties; and contacting the first and second polymers under conditions where the hydroxamic acid and boronic acid moieties undergo a reaction to provide a boronate ester. In another example, disclosed is a method of making a polymeric composition that comprises contacting a polymer comprising one or more hydroxamic acid moieties with a linker agent comprising two or more boronic acid moieties, wherein the hydroxamic acid and boronic acid moieties undergo a reaction to provide the polymeric composition. In still another example, disclosed is a method of making a polymeric composition that comprises contacting a polymer comprising one or more boronic acid moieties with a linker agent comprising two or more hydroxamic acid moieties, wherein the hydroxamic acid and boronic acid moieties undergo a reaction to provide the polymeric composition. In a further example, disclosed is a method of making a polymeric composition that comprises contacting a polymer comprising one or more hydroxamic acid moieties, one or more boronic acid moieties, or both with a linker agent comprising two or more boronic acid moieties, two or more hydroxamic acid moieties, or both, wherein the hydroxamic acid and boronic acid moieties undergo a reaction to provide the polymeric composition. In the disclosed methods, a reaction takes place between the reactive moieties on the polymers or on the polymers and the linking agent to result in a covalent attachment between the remaining polymer residues or between the remaining polymer residue and the remaining linking agent residue.

In many examples the reaction conditions for preparing the disclosed polymer compositions can be mild, at a pH of from about 0 to about 10, from about 1 to about 7, from about 2 to about 6, from about 3 to about 5, or from about 4 to about 8. In another example, the pH can be neutral or physiological pH. In another example the reaction can occur in aqueous media or in biological fluids. For example, the composition or components thereof can be dissolved in water, which may also contain water-miscible solvents including, but not limited to, dimethylformamide, dimethylsulfoxide, and alcohols, diols, or glycerols. In other examples the reaction can occur at from about minus 4° C. to about 90° C., from about 4° C. to about 80° C., from about 4° C. to about 70° C., from about 4° C. to about 60° C., from about 4° C. to about 50° C., from about 4° C. to about 40° C., from about 20° to about 40° C., or from about 25° C. to about 37° C. In another particular example the reaction occurs at about 37° C. Further, the reaction between the hydroxamic acid and boronic acid moiety can occur in the presence of cells, biomolecules, tissues, and salts, such as are present in a biological system. Still further the reaction can occur in non-aqueous media.

In the disclosed methods, any of the polymers and any of the linking agents disclosed herein can be used, including any of the hydroxamic acid and boronic acid moieties disclosed herein.

In other examples, the covalent crosslinks formed according to the disclosed methods can be reversed under strong acid conditions (pH<4). This unique feature of the disclosed polymeric compositions can be desirable for certain applications. But by adding primary and secondary amines into the boronic prepolymer composition, the pKa of the boronic acid moiety will be lowered, thus effectively stabilizing the covalent bond formation at even lower pH.

It is also contemplated that crosslinking the hydroxamic acid and boronic acid moieties can be performed in the presence of a sugar. In many instances the crosslinking reaction can be quite rapid. And in certain circumstances or applications rapid crosslinking may not be desirable. Thus, disclosed herein are methods of controlling the crosslinking by performing it in the presence of a sugar. Further the disclosed polymeric compositions can further comprise one or more sugars.

Additional Crosslinking

It is also contemplated that the crosslinking disclosed herein can be used along with other crosslinking chemistries. For example, the disclosed polymeric compositions can contain crosslinking produced with other crosslinking chemistries before or after the hydroxamic acid-boronic acid based crosslinking.

For example, a polycarbonyl linker agent can react with any of the polymers disclosed herein. The term "polycarbonyl linker agent" is defined herein as a compound that possesses two or more groups represented by the formula $A^1C(O)$—, where $A^1$ is hydrogen, lower alkyl, or $OA^2$, where $A^2$ is a group that results in the formation of an activated ester. In one aspect, any of the polymers can be further crosslinked with a polyaldehyde. A polyaldehyde is a compound that has two or more aldehyde groups. In one aspect, the polyaldehyde is a dialdehyde compound. In one example, any compound possessing two or more aldehyde groups can be used as the polyaldehyde linker agent. In another example, the polyaldehyde can be substituted or unsubstituted alkyl, alkenyl, alkynyl, cycloalkyl, cycloalkenyl, cycloalkynyl, ether, polyether, polyalkylene, ester, polyester, aryl, heteroaryl, and the like. In yet another example, the polyaldehyde can contain a polysaccharyl group or a polyether group. In a further aspect, the polyaldehyde can be a dendrimer or peptide. In one example, a polyether dialdehyde such as poly(ethylene glycol) propiondialdehyde (PEG) is useful in the compositions and methods described herein. PEG can be purchased from many commercial sources, such as Shearwater Polymers, Inc. (Huntsville, Ala.). The polyaldehyde can be glutaraldehyde in another example.

In another example, when the polycarbonyl compound is a polyaldehyde, the polyaldehyde can be prepared by the oxidation of terminal polyols or polyepoxides possessing two or more hydroxy or epoxy groups, respectively, using techniques known in the art.

The method of crosslinking generally involves reacting the polymer or polymeric composition with the polycarbonyl linker agent in the presence of a solvent.

In one aspect, the reaction solvent is water. In addition, small amounts of water miscible organic solvents, such as an alcohol or DMF or DMSO, can be used as well. In one aspect, crosslinking can be performed at room temperature, for example, 25° C., but the crosslinking reaction can be performed within a range of temperatures from below about 4° C. to above about 90° C. but typically would be performed at from about 4° C. to about 60° C., more typically from about 4° C. to about 50° C., and more typically at about 4° C., or about, 30° C., or about 37° C. The reaction will also work at a variety of pHs, for example, pH from about 3 to about 10, or pH from about 4 to about 9, or pH from about 5 to about 8, or at neutral pH.

Functionalization of the Polymer Compositions

In addition to reaction between the hydroxamic acid moieties and the boronic acid moieties to form a bond in the disclosed polymer compositions, it can be desired that some of the reactive moieties not react so that they can be available for subsequent or orthogonal coupling reactions with other components, e.g., pharmaceutical compounds, markers, dyes, targeting moieties, DNA probes, etc. Also contemplated herein are polymers and/or linking agents that contain a hydroxamic acid and/or boronic acid moiety, in addition to some other reactive moiety, e.g., a cycloaddition reactive moiety. In this way the disclosed polymer compositions can be crosslinked with the hydroxamic acid-boronic acid moieties, leaving the other reactive moieties (e.g., photoreactive sites) free to undergo a reaction with another component. For example, during or after a reaction between a hydroxamic acid moiety and a boronic acid moiety to crosslink the disclosed polymeric compositions, additional reactive moieties can cyclize with other components (e.g., cells, biomolecules, probes, labels, tags, etc.) to link them to the polymer composition. In a likewise fashion, the polymeric compositions can be attached to a solid support, such as glass or plastic, with additional reactive moieties (e.g., cycloaddition reactive moieties) that can be present on the disclosed compositions.

It is also contemplated that the polymer compositions can contain additional functionality other than hydroxamic acid and boronic acid moieties, which can be used to couple other compounds to the polymeric compositions. For example, a bioactive agent can be linked to the polymeric composition through an ether, imidate, thioimidate, ester, amide, thioether, thioester, thioamide, carbamate, disulfide, hydrazide, hydrazone, oxime ether, oxime ester, or and amine linkage.

In some specific examples, a polymeric composition as disclosed herein can be modified with one or more different groups so that the composition forms a covalent bond with a bioactive agent or a solid support. In one example, if the bioactive agent or solid support has an amino group, it can react with one or more groups on the polymeric composition to form a covalent or non-covalent bond. For example, the amino group on the bioactive agent or support can react with a carboxymethyl-derivatized hydrogel such as carboxymethyl dextran to produce a new covalent bond.

In one example, the polymeric composition can be a hydrogel possessing one or more groups that can form covalent and/or non-covalent attachments to another component (e.g., a biomolecules or bioactive agent). For example, the hydrogel layer can comprise one or more cationic groups or one or more groups that can be converted to a cationic group. Examples of such groups include, but are not limited to, substituted or unsubstituted amino groups. In one example, when the hydrogel possesses cationic groups, the hydrogel can attach to components that possess negatively-charged groups to form electrostatic interactions. Conversely, the hydrogel can possess groups that can be converted to anionic groups (e.g., carboxylic acids or alcohols), wherein the hydrogel can electrostatically attach to positively-charged components. Also, the hydrogel can possess one or more groups capable of forming covalent bonds with the other component. Thus, it is contemplated that the hydrogel can form covalent and/or non-covalent bonds with the component.

Anti-Adhesion Polymeric Compositions

In some particular examples, the disclosed polymeric compositions can be further coupled to an anti-adhesion compound and/or a prohealing compound. The term "anti-adhesion compound," as referred to herein, is defined as any compound that prevents cell attachment, cell spreading, cell growth, cell division, cell migration, or cell proliferation. In some examples, compounds that induce apoptosis, arrest the cell cycle, inhibit cell division, and stop cell motility can be used as the anti-adhesion compound. Examples of anti-adhesion compounds include, but are not limited to, anti-cancer drugs, anti-proliferative drugs, PKC inhibitors, ERK or MAPK inhibitors, cdc inhibitors, antimitotics such as colchicine or taxol, DNA intercalators such as adriamycin or camptothecin, or inhibitors of PI3 kinase such as wortmannin or LY294002. In one example, the anti-adhesion compound is a DNA-reactive compound such as mitomycin C. In another example, any of the oligonucleotides disclosed in U.S. Pat. No. 6,551,610, which is incorporated by reference in its entirety, can be used as the anti-adhesion compound. In another example, any of the anti-inflammatory drugs described below can be the anti-adhesion compound. Examples of anti-inflammatory compounds include, but are not limited to, methyl prednisone, low dose aspirin, medroxy progesterone acetate, and leuprolide acetate.

The formation of anti-adhesion polymeric compositions involves reacting the anti-adhesion compound with the polymer composition to form a new covalent bond. In one example, the anti-adhesion compound possesses a group that is capable of reacting with the polymeric composition (either through crosslinking with boronic acid moieties and/or hydroxamic acid moieties or through some other mechanism). The group present on the anti-adhesion compound that can react with the polymeric composition can be naturally-occurring or the anti-adhesion compound can be chemically modified to add such a group. In another example, the polymeric composition can be chemically modified so that it is more reactive with the anti-adhesion compound.

In some examples, the anti-adhesion polymeric composition can be formed by crosslinking the anti-adhesion compound with the polymeric composition. In one example, the anti-adhesion compound and the polymeric composition each possess at least one crosslinking reactive moiety (e.g., boronic acid and hydroxamic acid moieties), which then can react with a linker agent having at least two crosslinking reactive moieties. Any of the crosslinking reactive moieties described herein can be used in this respect. In one example, the linker agent is a polyethylene glycol diboronate or a polyethylene glycol dihydroxamic acid.

The amount of the anti-adhesion compound relative the amount of the polymer composition can vary. In one example, the volume ratio of the anti-adhesion compound to the polymeric composition is from 99:1, 90:10, 80:20, 70:30, 60:40, 50:50, 40:60, 30:70, 20:80, 10:90, or 1:99. In one example, the anti-adhesion compound and the polymeric composition can react in air and are allowed to dry at room temperature. The resultant compound can then be rinsed with water to remove any unreacted anti-adhesion compound. The composite can optionally contain unreacted (i.e., free) anti-adhesion compound. The unreacted anti-adhesion compound can be the same or different anti-adhesion compound that is covalently bonded to the polymeric composition.

The anti-adhesion polymeric composition can also be composed of a prohealing compound. The term "prohealing compound" as defined herein is any compound that promotes cell growth, cell proliferation, cell migration, cell motility, cell adhesion, or cell differentiation. In one example, the prohealing compound includes a protein or synthetic polymer. Proteins useful in the methods described herein include, but are not limited to, an extracellular matrix protein, a chemically-modified extracellular matrix protein, or a partially hydrolyzed derivative of an extracellular matrix protein. The proteins can be naturally occurring or recombinant polypeptides possessing a cell interactive domain. The protein can also be mixtures of proteins, where one or more of the proteins are modified. Specific examples of proteins include, but are not limited to, collagen, elastin, decorin, laminin, or fibronectin.

In another example, the prohealing compound can be any of the supports disclosed in U.S. Pat. No. 6,548,081 B2, which is incorporated by reference in its entirety. In one example, the prohealing compound includes crosslinked alginates, gelatin, collagen, crosslinked collagen, collagen derivatives, such as, succinylated collagen or methylated collagen, cross-linked hyaluronan, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(L-glutamic acid), poly (D-glutamic acid), polyacrylic acid, poly(DL-glutamic acid), poly(L-aspartic acid), poly(D-aspartic acid), poly(DL-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin. In another example, highly crosslinked HA can be the prohealing compound.

In another example, the prohealing compound can be a polysaccharide. In one aspect, the polysaccharide has at least one group, such as a carboxylic acid group or the salt or ester thereof that can react with a boronic acid and/or hydroxamic acid crosslinking reactive moiety as disclosed herein. In one example, the polysaccharide is a glycosaminoglycan (GAG). Any of the glycosaminoglycans described above can be used in this example. In another example, the prohealing compound is hyaluronan.

In some examples, the prohealing compound can be crosslinked with the polymeric composition. In one example, the prohealing compound and the polymeric composition each possess at least one crosslinking reactive moiety, which then can react with another polymer or linker agent having at least two crosslinking reactive moieties. Any of the crosslinking reactive moieties described herein can be used in this respect (e.g., boronic acid and/or hydroxamid acid moieties).

The anti-adhesion polymeric compositions can optionally contain a second prohealing compound. In one example, the second prohealing compound can be a growth factor. Any substance or metabolic precursor which is capable of promoting growth and survival of cells and tissues or augmenting the functioning of cells is useful as a growth factor. Examples of growth factors include, but are not limited to, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like. The amount of growth factor incorporated into the composite will vary depending upon the growth factor and prohealing compound selected as well as the intended end-use of the anti-adhesion polymeric composition.

Any of the growth factors disclosed in U.S. Pat. No. 6,534,591 B2, which is incorporated by reference in its entirety, can be used in this respect. In one example, the growth factor includes transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); inhibins (for example, Inhibin A, Inhibin B); growth differentiating factors (for example, GDF-1); and Activins (for example, Activin A, Activin B, Activin AB).

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

In another example, the addition of a linker agent can be used to couple the polymeric composition with the prohealing compound. In one example, when the polymeric composition and the prohealing compound possess crosslinking reactive moieties, a linker agent having at least two crosslinking reactive moieties can be used to couple the two compounds. Suitable crosslinking reactive moieties can include the hydroxamic acid and boronic acid moieties disclosed herein.

In further examples, the disclosed compositions can be formed into filaments. This can be done by, for example, electrospinning or extrusion. As such, contemplated herein are methods of forming filaments by electrospinning or extruding the polymeric compositions disclosed herein.

Still further, disclosed herein are methods of fabricating articles from the disclosed polymeric compositions. The particular methods of fabrication will depend on the particular article being made. Some examples include electrospinning, injection molding, melt processing, and thermally extruding the disclosed polymeric compositions.

Methods of Use

Any of the compounds, composites, compositions, and methods described herein can be used for a variety of uses. For example, the disclosed compositions can be used for drug delivery, small molecule delivery, wound healing, burn injury healing, and tissue regeneration, to name but a few uses. The disclosed compositions and methods are useful for situations which benefit from a hydrated, pericellular environment in which assembly of other matrix components, presentation of growth and differentiation factors, cell migration, or tissue regeneration are desirable.

The disclosed polymeric compositions can be used injectable drug delivery applications, including vaginal microbicides (anti-HIV drug delivery systems for the prevention of HIV infection). Other relevant applications include, but are not limited to, tissue engineering, cell encapsulation therapies, topical dressings, hydrogel coating of implantable biomedical devices, and artificial extracellular matrices. The biocompatible crosslinking chemistry disclosed herein can provide an effective alternative for all alginate hydrogel applications. Furthermore, the disclosed polymeric compositions can have beneficial use in anti-thrombosis applications (e.g., hydrogel coating of blood-contacting biomedical devices).

In another contemplated use, the disclosed polymeric compositions that are pH sensitive can be used to deliver anti-HIV agents to the naturally acidic vaginal milieu and utilize a pH-responsive trigger to block viral transport across the gel. These pH-sensitive compositions can also be suitable for other biological applications in which similar acidic changes occur, such as for lysosomal and gastric drug delivery systems. Moreover, the disclosed polymeric compositions are highly versatile at neutral pH; these compositions can be engineered to form either dynamic semisolids for use in blood-based injectable drug delivery, cell encapsulation and coating implantable biomedical devices, or rigid, highly crosslinked hydrogels that can be effective for applications like tissue engineering and moldable polymeric constructs. In this sense, the disclosed polymeric compositions can be used to deliver at least one bioactive agent in an acidic environment, comprising contacting the acidic environment with the polymeric composition of any of claims. By acidic environment is meant an environment with a pH of less than or equal to about 6.9, 6.5, 6.0, 5.5, 5.0, 4.5, 4.0, 3.5, 3.0, 2.5, 2.0, 1.5, 1.0, or 0.5, where any of the stated values can form an upper or lower endpoint. The disclosed polymeric compositions can be designed to fit the demands of most physiological conditions.

In many examples, the disclosed polymeric compositions and components can be placed directly in or on any biological system without purification. Examples of sites the disclosed compositions can be placed include, but are not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the cul-de-sac of the eye, and the like; the peritoneal cavity and organs contained within, and other sites into or onto which the compounds can be placed including a skin surface defect such as a cut, scrape or burn area. Alternatively, the disclosed compositions can be used to extend the viability of damaged skin. The disclosed compositions can be biodegradable and naturally occurring enzymes can act to degrade them over time. The disclosed compositions can be "bioabsorbable" in that the disclosed compositions can be broken down and absorbed within the biological system, for example, by a cell, tissue and the like. Additionally, the disclosed compositions that have not been rehydrated can be applied to a biological system to absorb fluid from an area of interest. Moreover, any residual, unreacted boronic acid moieties and/or hydroxamic acid moieties present in the disclosed polymeric compositions can interact with sugar and/or diol moieties found in mucus and cell surfaces. Thus, the disclosed polymeric compositions can have desirable mucoadhesion and/or bioadhesion properties.

The disclosed compositions can be used in a number of different surgical procedures. In one example, the disclosed compositions can be used in any of the surgical procedures disclosed in U.S. Pat. Nos. 6,534,591 B2 and 6,548,081 B2, which are incorporated by reference in their entireties. In one example, the disclosed compositions can be used in cardiosurgery and articular surgery; abdominal surgery where it is important to prevent adhesions of the intestine or the mesentery; operations performed in the urogenital regions where it is important to ward off adverse effects on the ureter and bladder, and on the functioning of the oviduct and uterus; and nerve surgery operations where it is important to minimize the development of granulation tissue. In surgery involving tendons, there is generally a tendency towards adhesion between the tendon and the surrounding sheath or other surrounding tissue during the immobilization period following the operation. In another example, the disclosed compositions can be used to prevent adhesions after laparascopic surgery, pelvic surgery, oncological surgery, sinus and craniofacial surgery, ENT surgery, or in procedures involving spinal dura repair.

In another example, the disclosed compositions can be used in ophthalmological surgery. In ophthalmological surgery, a biodegradable implant could be applied in the angle of the anterior chamber of the eye for the purpose of preventing the development of synechiae between the cornea and the iris; this applies especially in cases of reconstructions after severe damaging events. Moreover, degradable or permanent implants are often desirable for preventing adhesion after glaucoma surgery and strabismus surgery.

The disclosed polymeric compositions can be used as intra-ocular lenses, either prefabricated or formed in situ (i.e. minimally invasive surgery). Currently, intraocular lenses are synthesized from a stiff polymer, polymethyl methacrylate, and are implanted in cataract patients after removal of cataract. However, the ability to adjust focus for near vision is lost after cataract surgery. Using the disclosed polymeric compositions, optically clear soft gels of desired refractive index can be synthesized that can provide the ability of natural accommodation to the patient. Additionally, as this system can be crosslinked in situ, the intraocular lenses can be formed in situ in the natural lens capsule in the eye after removal of the cataract (opaque lens) without causing damage to the natural lens capsule.

In another example, the outstanding biocompatibility characteristic of the disclosed polymeric compostions with living tissue, in combination with properties such as transparency, good optics, shape stability, inertness to chemicals and bacteria, high water content, high oxygen permeability, etc., can make the disclosed polymeric compositions suitable for the production of daily wear soft contact lenses.

In another example, the disclosed compositions can be used in the repair of tympanic membrane perforations (TMP). The tympanic membrane (TM) is a three-layer structure that separates the middle and inner ear from the external environment. These layers include an outer ectodermal portion composed of keratinizing squamous epithelium, an intermediate mesodermal fibrous component and an inner endodermal mucosal layer. This membrane is only 130 μm thick but provides important protection to the middle and inner ear structures and auditory amplification.

TMP is a common occurrence usually attributed to trauma, chronic otitis media or from PE tube insertion. Blunt trauma resulting in a longitudinal temporal bone fracture is classically associated with TMP. More common causes include a slap to the ear and the ill-advised attempt to clean an ear with a cotton swab or sharp instrument.

Any of the disclosed compositions can be administered through the tympanic membrane without a general anesthetic and still provide enhanced wound healing properties. In one aspect, the disclosed compositions can be injected through the tympanic membrane using a cannula connected to syringe.

In another example, the disclosed compositions can be used as a postoperative wound barrier following endoscopic sinus surgery. Success in functional endoscopic sinus surgery (FESS) is frequently limited by scarring, which narrows or even closes the surgically widened openings. Spacers and tubular stents have been used to temporarily maintain the opening, but impaired wound healing leads to poor long-term outcomes. The use of any compounds, composites, and compositions described herein can significantly decrease scar contracture following maxillary sinus surgery.

In another example, the disclosed compositions can be used for the augmentation of soft or hard tissue. In another example, the disclosed compositions can be used to coat articles such as, for example, a surgical device, a prosthetic, or an implant (e.g., a stent). In another example, the disclosed compositions can be used to treat aneurisms.

The disclosed compositions can be used as a carrier and delivery device for a wide variety of releasable bioactive agents having curative or therapeutic value for human or non-human animals. Any of the bioactive agents described herein can be used in this respect. Many of these substances which can be carried by the disclosed compositions are discussed herein.

Included among bioactive agents that are suitable for incorporation into the disclosed compositions are therapeutic drugs, e.g., anti-inflammatory agents, anti-pyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues and so forth. The bioactive agent is added in pharmaceutically active amounts.

The rate of drug delivery depends on the hydrophobicity of the molecule being released. For example, hydrophobic molecules, such as dexamethazone and prednisone are released slowly from the composition as it swells in an aqueous environment, while hydrophilic molecules, such as pilocarpine, hydrocortisone, prednisolone, cortisone, diclofenac sodium, indomethacin, 6∝-methyl-prednisolone and corticosterone, are released quickly. The ability of the compositions to maintain a slow, sustained release of steroidal anti-inflammatories makes the compounds described herein extremely useful for wound healing after trauma or surgical intervention.

In certain methods the delivery of molecules or reagents related to angiogenesis and vascularization are achieved. Disclosed are methods for delivering agents, such as VEGF, that stimulate microvascularization. Also disclosed are methods for the delivery of agents that can inhibit angiogenesis and vascularization, such as those compounds and reagents useful for this purpose disclosed in but not limited to U.S. Pat. No. 6,174,861 for "Methods of inhibiting angiogenesis via increasing in vivo concentrations of endostatin protein;" U.S. Pat. No. 6,086,865 for "Methods of treating angiogenesis-induced diseases and pharmaceutical compositions thereof;" U.S. Pat. No. 6,024,688 for "Angiostatin fragments and method of use;" U.S. Pat. No. 6,017,954 for "Method of treating tumors using O-substituted fumagillol derivatives;" U.S. Pat. No. 5,945,403 for "Angiostatin fragments and method of use;" U.S. Pat. No. 5,892,069 "Estrogenic compounds as anti-mitotic agents;" for U.S. Pat. No. 5,885,795 for "Methods of expressing angiostatic protein;" U.S. Pat. No. 5,861,372 for "Aggregate angiostatin and method of use;" U.S. Pat. No. 5,854,221 for "Endothelial cell proliferation inhibitor and method of use;" U.S. Pat. No. 5,854,205 for "Therapeutic antiangiogenic compositions and methods;" U.S. Pat. No. 5,837,682 for "Angiostatin fragments and method of use;" U.S. Pat. No. 5,792,845 for "Nucleotides encoding angiostatin protein and method of use;" U.S. Pat. No. 5,733,876 for "Method of inhibiting angiogenesis;" U.S. Pat. No. 5,698,586 for "Angiogenesis inhibitory agent;" U.S. Pat. No. 5,661,143 for "Estrogenic compounds as anti-mitotic agents;" U.S. Pat. No. 5,639,725 for "Angiostatin protein;" U.S. Pat. No. 5,504,074 for "Estrogenic compounds as anti-angiogenic agents;" U.S. Pat. No. 5,290,807 for "Method for regressing angiogenesis using o-substituted fumagillol derivatives;" and U.S. Pat. No. 5,135,919 for "Method and a pharmaceutical composition for the inhibition of angiogenesis" which are herein incorporated by reference for the material related to molecules for angiogenesis inhibition.

In one example, the bioactive agent is pilocarpine, hydrocortisone, prednisolone, cortisone, diclofenac sodium, indomethacin, 6∝-methyl-prednisolone, corticosterone, dexamethasone and prednisone. However, methods are also provided wherein delivery of a bioactive agent is for a medical purpose selected from the group of delivery of contraceptive agents, treating postsurgical adhesions, promoting skin growth, preventing scarring, dressing wounds, conducting viscosurgery, conducting viscosupplementation, engineering or tissue.

In one example, the disclosed compositions can be used as a satiety agent. That is, the disclosed compositions that swell in acidic pH can be formulated as an oral dosage form (e.g., tablet, capsule, gel cap, syrup, powder, etc). When ingested, the low pH of the stomach causes the composition to swell and the subject feels satisfied. It is also contemplated that bioactive agents that are known for use as satiety agents can be incorporated, encapsulated, or bound to the disclosed compositions and released upon ingestion.

In one example, the disclosed compositions can be used for the delivery of living cells to a subject. Any of the living cells described herein can be used in the respect. In one example, the living cells are part of a prohealing compound. In another example, the disclosed compositions can be used to support the growth of a variety of cells including, but not limited to, tumor cells, fibroblasts, chondrocytes, stem cells (e.g., embryonic, preadipocytes, mesenchymal, cord blood derived, bone marrow), epithelial cells (e.g., breast epithelial cells, intestinal epithelial cells), cells from neural lineages (e.g., neurons, astrocytes, oligodendrocytes, and glia), cells derived from the liver (e.g., hepatocytes), endothelial cells (e.g., vascular endothelial), cardiac cells (e.g., cardiac myocytes), muscle cells (e.g., skeletal or vascular smooth muscle cells), or osteoblasts. Alternatively, cells may be derived from cell lines or a primary source (e.g., human or animal), a biopsy sample, or a cadaver.

In one example, the disclosed compositions can be used for the delivery of growth factors and molecules related to growth factors. Any of the growth factors described herein are useful in this aspect. In one example, the growth factor is part of a prohealing compound.

In one example, described herein are methods for reducing or inhibiting adhesion of two tissues in a surgical wound in a subject by contacting the wound of the subject with any of the disclosed compositions. Not wishing to be bound by theory, it is believed that the disclosed compositions will prevent tissue adhesion between two different tissues (e.g., organ and skin tissue). It is desirable in certain post-surgical wounds to prevent the adhesion of tissues in order to avoid future complications.

The disclosed compositions provide numerous advantages. For example, the disclosed compositions can provide a post-operative adhesion barrier that is at least substantially resorbable and, therefore, does not have to be removed surgically at a later date. Another advantage is that the disclosed compositions are also relatively easy to use, can, in some instances, be sutured, and tend to stay in place after it is applied.

In another example, described herein are methods for improving wound healing in a subject in need of such improvement by contacting any of the disclosed compositions with a wound of a subject in need of wound healing improvement. Also provided are methods to deliver at least one bioactive agent to a subject in need of such delivery by contacting any of the disclosed compositions with at least one tissue capable of receiving said bioactive agent.

The disclosed compositions can be used for treating a wide variety of tissue defects in an animal, for example, a tissue with a void such as a periodontal pocket, a shallow or deep cutaneous wound, a surgical incision, a bone or cartilage defect, bone or cartilage repair, vocal fold repair, and the like. For example, the disclosed compositions can be in the form of a hydrogel film. The hydrogel film can be applied to a defect in bone tissue such as a fracture in an arm or leg bone, a defect in a tooth, a cartilage defect in the joint, ear, nose, or throat, and the like. The hydrogel film composed of the disclosed compositions can also function as a barrier system for guided tissue regeneration by providing a surface on or through which the cells can grow. To enhance regeneration of a hard tissue such as bone tissue, the hydrogel film can provide support for new cell growth that can replace the matrix as it becomes gradually absorbed or eroded by body fluids.

The disclosed compositions can be delivered onto cells, tissues, and/or organs, for example, by injection, spraying, squirting, brushing, painting, coating, and the like. Delivery can also be via a cannula, catheter, syringe with or without a needle, pressure applicator, pump, and the like. The disclosed compositions can be applied onto a tissue in the form of a film, for example, to provide a film dressing on the surface of the tissue, and/or to adhere to a tissue to another tissue or hydrogel film, among other applications.

In one example, the disclosed compositions can be administered via injection. For many clinical uses, when the disclosed compositions are in the form of a hydrogel film, injectable hydrogels can be used. An injectable hydrogel can be formed into any desired shape at the site of injury. Because the initial hydrogels can be sols or moldable putties, the systems can be positioned in complex shapes and then subsequently crosslinked to conform to the required dimensions. Also, the hydrogel would adhere to the tissue during gel formation, and the resulting mechanical interlocking arising from surface microroughness would strengthen the tissue-hydrogel interface. Further, introduction of an in situ-crosslinkable hydrogel could be accomplished using needle or by laparoscopic methods, thereby minimizing the invasiveness of the surgical technique.

The disclosed compositions can be used to treat periodontal disease, gingival tissue overlying the root of the tooth can be excised to form an envelope or pocket, and the composition delivered into the pocket and against the exposed root. The compounds, composites, and compositions can also be delivered to a tooth defect by making an incision through the gingival tissue to expose the root, and then applying the material through the incision onto the root surface by placing, brushing, squirting, or other means.

When used to treat a defect on skin or other tissue, the disclosed compositions can be in the form of a hydrogel film that can be placed on top of the desired area. In this aspect, the hydrogel film is malleable and can be manipulated to conform to the contours of the tissue defect.

The disclosed compositions can be applied to an implantable device such as a suture, claps, stents, prosthesis, catheter, metal screw, bone plate, pin, a bandage such as gauze, and the like, to enhance the compatibility and/or performance or function of an implantable device with a body tissue in an implant site. The disclosed compositions can be used to coat the implantable device. For example, the disclosed compositions could be used to coat the rough surface of an implantable device to enhance the compatibility of the device by providing a biocompatible smooth surface which reduces the occurrence of abrasions from the contact of rough edges with the adjacent tissue. The disclosed compositions can also be used to enhance the performance or function of an implantable device. For example, when the disclosed compositions are a hydrogel film, the hydrogel film can be applied to a gauze bandage to enhance its compatibility or adhesion with the tissue to which it is applied. The hydrogel film can also be applied around a device such as a catheter or colostomy that is inserted through an incision into the body to help secure the catheter/colosotomy in place and/or to fill the void between the device and tissue and form a tight seal to reduce bacterial infection and loss of body fluid.

In one example, the disclosed compositions that comprise, for example, PLURONICS™ can couple to GAGs such as, for example, hyaluronan or heparin, and self-assemble into hydrogels. Alternatively, solutions of the disclosed compositions and GAGs can be coated on a hydrophobic surface such as, for example, a medical device. For example, heparin can be coupled with a hydrophilic polymer comprising a PLURONIC™ wherein the resultant gel possesses desirable growth-binding factor capabilities but does not possess anticoagulant properties associated with heparin. Not wishing to be bound by theory, the PLURONIC™ portion of the hydrogel can prevent coagulation, which is undesirable side-effect of heparin.

It is understood that the disclosed compositions can be applied to a subject in need of tissue regeneration. For example, cells can be incorporated into the disclosed compositions herein for implantation. Examples of subjects that can be treated with the disclosed compositions include mammals such as mice, rats, cows or cattle, horses, sheep, goats, cats, dogs, and primates, including apes, chimpanzees, orangatangs, and humans. In another aspect, the disclosed compositions can be applied to birds.

When being used in areas related to tissue regeneration such as wound or burn healing, it is not necessary that the disclosed compositions and methods eliminate the need for one or more related accepted therapies. It is understood that any decrease in the length of time for recovery or increase in the quality of the recovery obtained by the recipient of the disclosed compositions and methods has obtained some benefit. It is also understood that some of the disclosed compositions and methods can be used to prevent or reduce fibrotic adhesions occurring as a result of wound closure as a result of trauma, such surgery. It is also understood that collateral affects provided by the disclosed compositions and methods are desirable but not required, such as improved bacterial resistance or reduced pain etc.

In one example, the disclosed compositions can be used to prevent airway stenosis. Subglottic stenosis (SGS) is a condition affecting millions of adults and children world-wide. Causes of acquired SGS range from mucosal injury of respiratory epithelia to prolonged intubation. Known risk factors of SGS in intubated subject include prolonged intubation, high-pressure balloon cuff, oversized endotracheal (ET) tube, multiple extubations or re-intubations, and gastro-esophageal reflux. There are also individuals in whom stenosis develops as a result of surgery, radiation, autoimmune disease, tumors, or other unexplained reasons.

While very diverse, the etiologies of SGS all have one aspect in common, narrowing of the airway resulting in obstruction. This narrowing most commonly occurs at the level of the cricoid cartilage due to its circumferential nature and rigidity. Such etiologies have been found in various SGS models: activation of chondrocytes and formation of fibrous scar, infiltration of polymorphonuclear leukocytes and chronic inflammatory cells with squamous metaplasia, and morphometric changes in airway lumen. Each presents a problem requiring immediate attention.

In another example, any of the disclosed compositions can be used as a 3-D cell culture. In one example, the hydrogel can be lyophilized to create a porous sponge onto which cells may be seeded for attachment, proliferation, and growth. It is contemplated that miniarrays and microarrays of 3-D hydrogels or sponges can be created on surfaces such as, for example, glass, and the resulting gel or sponge can be derived from any of the compounds or compositions described herein. The culture can be used in numerous embodiments including, but not limited to, determining the efficacy or toxicity of experimental therapeutics.

Still other uses of the disclosed polymeric compositions include delivery of bioactive agents (e.g., microbicides, spermacides, anti-inflamatory agents, and the like) to the vagina. For example, the disclosed polymeric compositions that contain a bioactive agent can be administered to the transmucosal and topical mucosal of the vagina by inserting a vaginal device containing or coated with the disclosed polymeric compositions. Suitable vaginal devices include, but are not limited to, a vaginal tampon, vaginal ring, vaginal strip, vaginal capsule, vaginal tablet, vaginal pessary, vaginal cup, vaginal film, or vaginal sponge. Further, the disclosed compositions can be applied directly to the vaginal mucosa in the form of a cream, lotion, or foam. In this regard, the disclosed compositions that are formed at higher pH (e.g., pH 7) but become viscous and/or dissolve at lower pH (e.g., vaginal pH of about 4) are particularly useful.

The vaginal route of delivery can permit extended, continuous, or pulsed delivery and administration of a bioactive agent without need to visit the doctor's office or hospital. Using the polymeric compositions alone or in combination with a vaginal device, the length of the drug delivery can be extended and the delivered dose can be lowered as the vaginal delivery by-passes the gastrointestinal tract and eliminates the need for intravenous administration with all its adverse effects and requirements.

In a further use of the disclosed polymeric compositions, they can be used to prepare a molded or extruded article. Methods of molding and extruding thermoplastic polymers are well known in the art. Such processes typically involve heating the polymer to a temperature where the polymer is molten. Then the molten polymer is extruded through a dye or injected into a mold and then cooled. With many of the polymeric compositions disclosed herein, the crosslinks are thermo-reversible. As such, a rise in temperature can break many of the crosslinks and render the disclosed polymeric compositions less viscous. In that more viscous state, they can be molded into an article through typical methods.

The disclosed polymeric compositions can also be incorporated into liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The disclosed polymeric compositions in liposome form can contain, in addition to any of active compounds disclosed herein, stabilizers, preservatives, excipients, and the like. Examples of suitable lipids are the phospholipids and the phosphatidyl cholines (lecithins), both natural and synthetic. Methods of forming liposomes are known in the art. See, e.g., Prescott, Ed., *Methods in Cell Biology*, Volume XIV, Academic Press, New York, p. 33 et seq., 1976, which is hereby incorporated by reference herein for its teachings of liposomes and their preparation. In other examples, the liposomes can be cationic liposomes (e.g., DOTMA, DOPE, DC cholesterol) or anionic liposomes. Liposomes can further comprise proteins to facilitate targeting a particular cell, if desired. Administration of a composition comprising a polymeric compositions compound and a cationic liposome can be administered to the blood afferent to a target organ or inhaled into the respiratory tract to target cells of the respiratory tract. Regarding liposomes, see, e.g., Brigham, et al., *Am J Resp Cell Mol Biol* 1:95-100, 1989; Felgner, et al., *Proc Natl Acad Sci USA* 84:7413-7, 1987; and U.S. Pat. No. 4,897,355, which are incorporated by reference herein for their teachings of liposomes. As one example, delivery can be via a liposome using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. Liposomes where the diffusion of the compound or delivery of the compound from the liposome is designed for a specific rate or dosage can also be used.

The disclosed compositions can be particularly useful as a gelatin substitute in a foodstuff. Thus, also contemplated herein are foodstuffs that comprise any of the polymeric compositions disclosed herein. By "foodstuff" is meant any article that can be consumed (e.g., eaten, drank, or ingested) by a subject. For example, the disclosed polymeric compositions can be loaded with nutrients, vitamins, minerals, trace elements, and other compounds that provide health benefits. These formulations can then be incorporated into a foodstuff. In some examples, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In other examples, the foodstuff is bread, tortillas, cereal, sausage, chicken, ice cream, yogurt, milk, salad dressing, rice bran, fruit juice, a dry beverage powder, rolls, cookies, crackers, fruit pies, or cakes. Upon ingestion of the foodstuff, the polymeric composition will be exposed to the acidic environment of the stomach, which can change the viscoelastic properties of the polymeric composition and release the embedded or encapsulated compound(s).

Still further, the disclosed polymeric compositions can be used to encapsulate or contain inks for printing applications. The compositions can be designed so that they will release the imbedded or encapsulated ink under a desired pH or temperature condition.

In still another example, the disclosed polymeric compositions can be incorporated into foams or gels to enhance their impact resistance and cushioning properties. Such shock-absorbant gels or foams (e.g., polyurethane or ethylvinylacetate foams) comprising the disclosed polymeric compositions can be used in pads, bumpers, cushions, mattresses, helments, gloves, shoes soles and inserts, impact-protective clothing, and the like.

Kits

In a further aspect, disclosed herein is a kit that includes (1) a polymer comprising at least one hydroxamic acid moiety and (2) a polymer comprising at least one boronic acid moiety. Also disclosed herein is a kit that includes (1) a polymer comprising at least one hydroxamic acid moiety and (2) a linking agent that comprises at least two boronic acid moieties. Further, disclosed herein is a kit that includes (1) a polymer comprising at least one boronic acid moiety and (2) a linking agent that comprises at least two hydroxamic acid moieties. In some examples, the polymer can be any polymer disclosed herein. The boronic acid moieties and hydroxamic acid moieties can be any such moiety disclosed herein. Further, the linker agent can be any of those disclosed herein. Use of the kit generally involves admixing components (1) and (2) together under conditions where a boronic acid moiety reacts with a hydroxamic acid moiety. Components (1) and (2) can be added in any order. For example, the polymer(s) and linker agent can be in separate containers (e.g., syringes or spray cans), with the contents being mixed using when they are expelled together (e.g., by syringe-to-syringe techniques or spraying through the nozzle of a spray can) just prior to delivery to the subject.

In another example, the polymeric composition and anti-adhesion and/or prohealing compounds can be used as a kit. For example, the polymeric composition and anti-adhesion and/or prohealing compounds are in separate syringes, with the contents being mixed using syringe-to-syringe techniques just prior to delivery to the subject. In this example, the polymeric composition and anti-adhesion and/or prohealing compounds can be extruded from the opening of the syringe by an extrusion device followed by spreading the mixture via spatula.

In another example, the polymeric composition and the anti-adhesion and/or prohealing compounds are in separate chambers of a spray can or bottle with a nozzle or other spraying device. In this example, the first compound and anti-adhesion and/or prohealing compounds do not actually mix until they are expelled together from the nozzle of the spraying device.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Polysciences Inc. (Warrington, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Example 1

Synthesis of Crosslinkable Polymers

Monomer Syntheses

Phenylboronic acid-functionalized monomer was synthesized by symmetric anhydride-mediated amidation of N-(3-aminopropyl)methacrylamide hydrochloride (APMA, Polysciences, Inc., Warrington, Pa.) with 4-carboxyphenylboronic acid (PBA, Frontier Scientific, Inc., Logan, Utah). This is shown below in Scheme 4:

Scheme 4

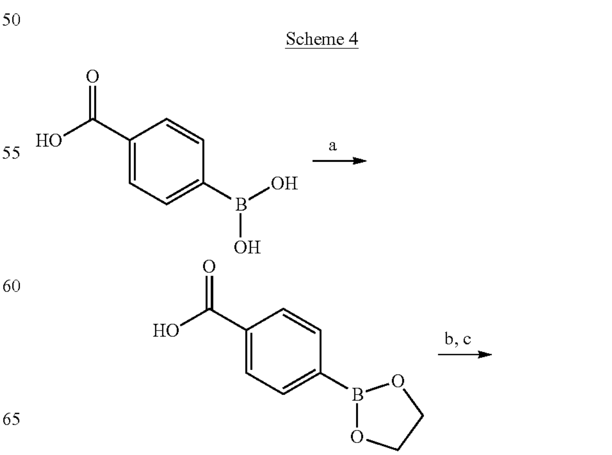

-continued

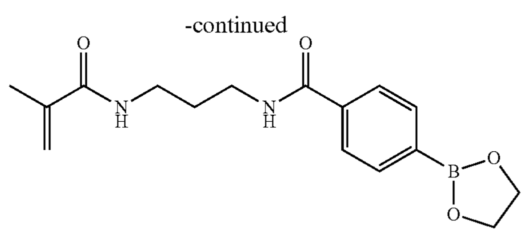

Briefly, PBA was boronate acid-protected using excess (10 eq.) ethylene glycol in dry 1,4-dioxane with molecular sieves present and refluxed for 3 hours at 110° C. (step a). The mixture was then filtered through Celite, concentrated in vacuo, and purified by flash chromatography (96:3:1 $CHCl_3$:MeOH:AcOH). Pure product (70-85% yield) was confirmed by $^1$H NMR. 2.2 eq. of protected PBA was then reacted at room temperature under nitrogen (gas) with 1.1 eq DIC in dry 5:2 DCM:DMF for 2 hours (step b) before adding by syringe a mixture of 1 eq. APMA, 2 eq. diisopropylethylamine (DIPEA) in minimal dry DMF (step c). The reaction was stirred overnight before concentrating, redissolving in DCM, filtering off precipitated urea side products, and final purification by flash chromatography (95:5 $CHCl_3$:MeOH). Pure product (73-74% yield) was confirmed by $^1$H NMR, MS, and TLC.

Salicylhydroxamic acid-functionalized monomer was synthesized using activated ester-mediated amidation of methacrylic acid and a salicylate intermediate followed by hydroxamidation of the vinyl intermediate. The salicylate intermediate, methyl 4-(aminomethyl)salicylate hydrochloride (MAMS), was synthesized similar to Stolowitz et al. (Stolowitz et al., *Bioconj Chem* 12(2):229-239, 2001). This is shown in Scheme 5:

Scheme 5

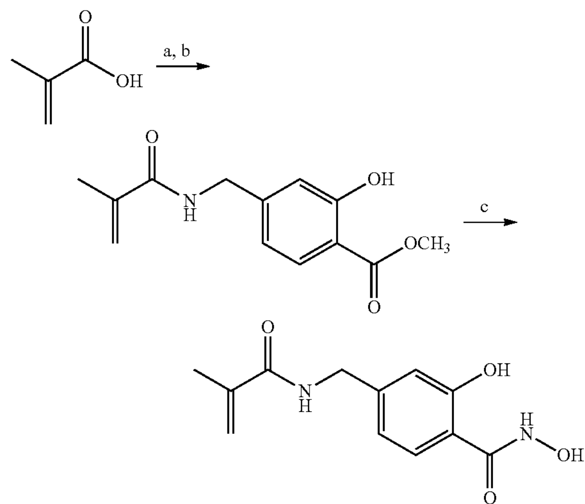

Briefly, the vinyl intermediate was synthesized by reacting 1 eq. of methacrylic acid with 1 eq. of 2-(1H-Benzotriazole-1-yl)-1,1,3,3-tetramethyluronium hexafluorophosphate (HBTU) and 1 eq. DIPEA in dry DCM and minimal DMF (step a). The reaction was stirred 2 hours at room temperature under nitrogen (gas) before a mixture of 1 eq. MAMS and 2 eq. DIPEA in dry DMF was added (step b). Following overnight stirring, the reaction mixture was concentrated and purified by flash chromatography (92:8 DCM:MeOH), giving 80% product yield. This intermediate product was then reacted with excess 50% aqueous hydroxylamine and 2 eq. DBU in DMF at room temperature for 24 h (step c). The final product was also purified by flash chromatography (92:8 DCM:MeOH), giving 80-95.6% product yield, and characterized by $^1$H NMR, MS, and TLC.

Non-functional vinyl monomer, 2-hydroxypropylmethacrylamide (HPMA), was synthesized by stirring a mixture 1 eq. of 1-amino-2-propanol and 1.5 eq. potassium carbonate in THF at minus 4° C., then adding 1 eq. of methacryloyl chloride dropwise to the chilled mixture, maintaining a reaction temperature below 2° C. After 30 minutes post-addition, the reaction mixture was filtered over Whatman paper, concentrated, redissolved in chloroform and filtered through a silica plug (initially collecting 100% chloroform fractions, followed by 1:9 isopropanol:chloroform fractions until all UV-quenching product was isolated). Following concentration, product was recrystallized from ethyl acetate. Pure product (44% yield) was confirmed by TLC and $^1$H NMR.

Prepolymer Syntheses

Phenylboronic acid prepolymers (pPBA) and salicylhydroxamic acid prepolymers (pSHA) were synthesized by free radical polymerization of either distilled acrylic acid (AA) or 2-hydroxypropylmethacrylamide (HPMA) and PBA-vinyl (boronic acid protected) or SHA-vinyl monomers. Polymerizations of varying degrees of functionalization (5-10 mol % functional monomer) were performed in 75 wt % DMF at 65° C. for 24 hours using 0.6 mol % azo-initiator (AIBN; azobisisobutyronitrile). Some of the polymers are shown below in Table 1:

TABLE 1

| | Theoretical Molar Ratio (Actual Molar Ratio*) (mol %) | | | | |
|---|---|---|---|---|---|
| Polymer | HPMA | AA | PBA vinyl | SHA vinyl | Mw/Mn (kD)** |
| p($HPMA_{90}$-$SHA_{10}$) | 90 (85.8) | — | — | 10 (14.2) | 239/164 |
| p($HPMA_{90}$-$PBA_{10}$) | 90 (92.6) | — | 10 (7.4) | — | 451/206 |
| p($AA_{90}$-$SHA_{10}$) | — | 90 (89.2) | — | 10 (10.8) | 173/86 |
| p($AA_{90}$-$PBA_{10}$) | — | 90 (91.5) | 10 (8.5) | — | 317/254 |

HPMA: 2-hydroxypropylmethacrylamide; AA: acrylic acid; PBA vinyl: N-[3-(2-methyl-acryloylamino)-propyl]-4-amidophenylboronic acid, pinacol ester; SHA vinyl: 4-[(2-methyl-acryloylamino)-methyl]-salicylhydroxamic acid. *Actual molar ratio was determined by $^1$H NMR in DMSO-d6 (Mercury 400 MHz spectrometer, Varian). **Mw and Mn were determined by GPC equipped with an aqueous column (PLaquagel-OH mixed, Polymer Labs) or an organic column (PLgel mixed-B, Polymer Labs), a multit-angle light scattering (BI-MwA, Brookhaven Instruments) and differential refractive index detectors (BI-DNDC, Brookhaven Instruments) and are represented as means of at least duplicate experiments (n=2-6) (GPC 1100, Agilent Technologies). GPC eluents used were either DDI water or HPLC-grade DMF at a flow rate of 0.75 mL/min at 30° C. Polymer samples were injected at a concentration of 0.5 mg/mL.

The boronic acid moieties on pPBA prepolymers were deprotected by acidifying the mixtures to pH<4 with 1 M HCl. Prepolymers were precipitated at least twice in acetone. Finally, prepolymers were dissolved in DDI water, filtered over 0.45 μm membranes and freeze-dried for at least 72 hours. Prepolymers (54-76% yield) were characterized by $^1$H NMR and GPC.

Example 2

Gelation Evolution by Dynamic Rheology pPBA and pSHA prepolymers (10 mol % functionalization each) were prepared at 100 mg/mL and 50 mg/mL in 1 M acetate buffer (pH 4). Equal volumes of matching pPBA and pSHA solutions were simultaneously pipetted onto the rheometer's Peltier plate. Immediately, the sample was mixed by preshearing for 30 seconds at an angular velocity of 2 rad/s. Gelation evolution was followed by running an oscillatory time sweep at 37° C. with a controlled 1 Hz oscillatory stress of 6.4 Pa.

Figure 2:
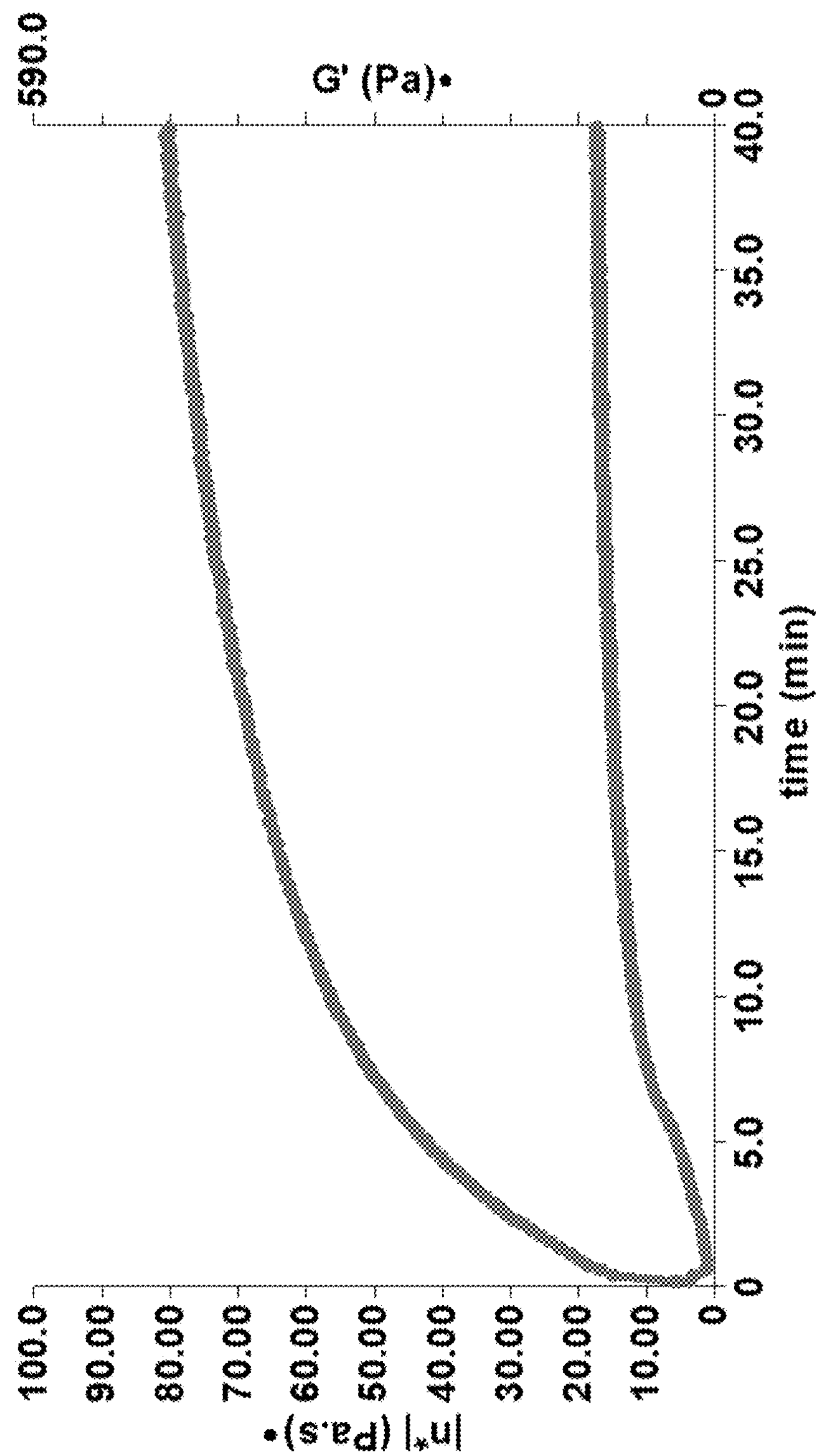
FIG. 2 is a graph obtained from rheological analysis of phenylboronic acid-salicylhydroxamic acid (PBA-SHA) hydrogel at pH 4. Specifically, the graph shows complex viscosity (|n*|, left y-axis) and storage modulus (G', right y-axis) versus time after mixing PBA and SHA prepolymer solutions. The prepolymers were dissolved separately in 1 M sodium acetate buffer (pH 4), either at 100 mg/mL (top line) or 50 mg/mL (bottom line), and were mixed 1:1 on the rheometer immediately before analysis.

Though gelation kinetics are dependent on the mixing conditions (i.e., diffusion limited), 100 mg/mL and 50 mg/mL formulations demonstrated maximum complex viscosities of 80 and 18 Pa·s, respectively (see FIG. 2).

Example 3

Shear Thinning and Recovery Properties by Dynamic Rheology

In order to evaluate shear thinning and gel recovery properties, the 100 mg/mL gel was subjected to an oscillatory strain sweep immediately following the time sweep (described above). Using a 1 Hz frequency at 37° C., strain was ramped stepwise from 1-200% in a log mode with 10 points per decade. The failed gel was allowed to relax for 10 minutes, at which time the strain sweep was repeated.

Figure 3:
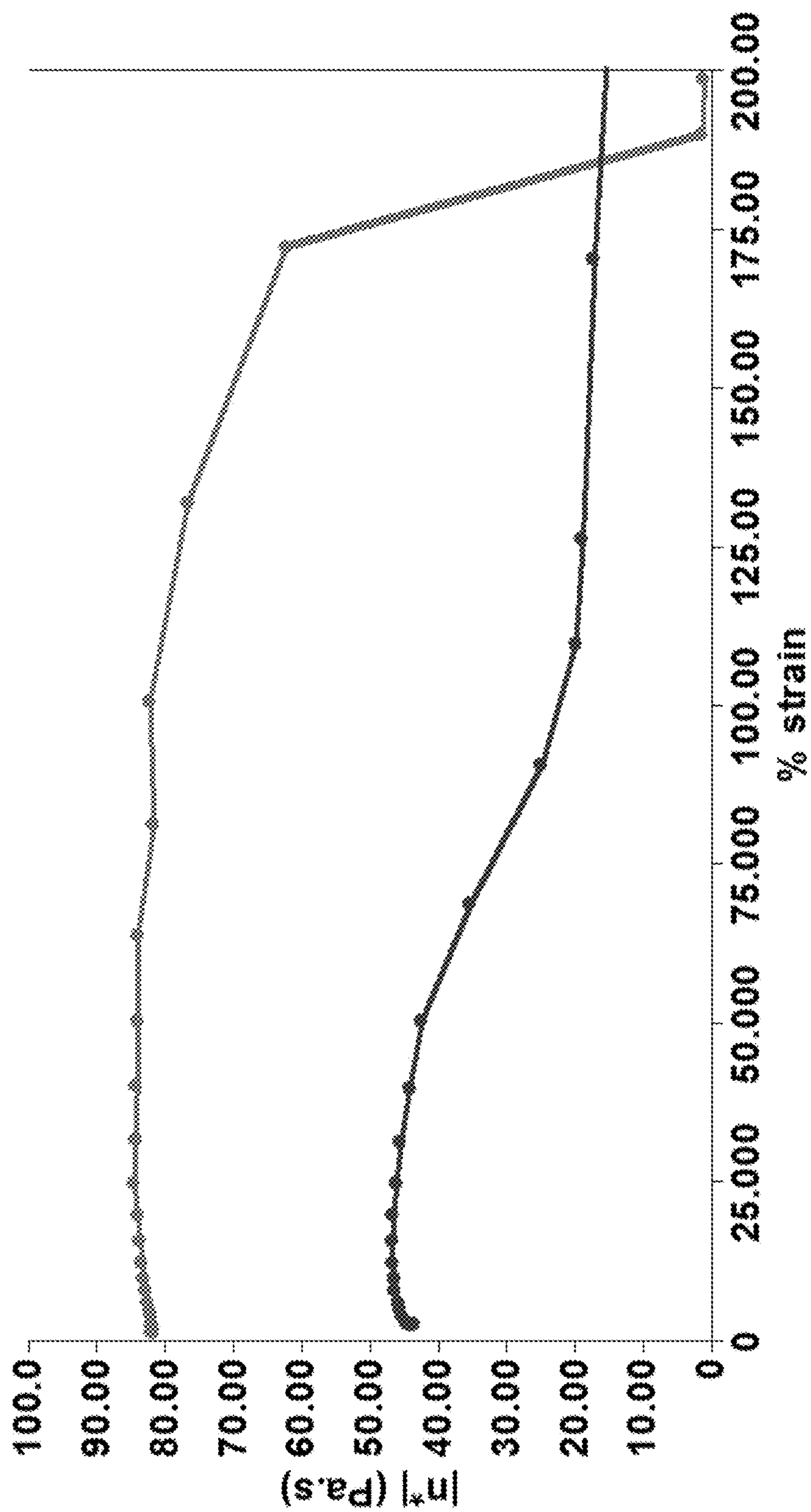
FIG. 3 is a graph obtained from rheological analysis of PBA-SHA hydrogel shear thinning and recovery properties at pH 4. Specifically, the graph shows complex viscosity (|n*|) versus percent strain after gelation of 100 mg/mL PBA-SHA polymers in 1 M sodium acetate buffer. The top line was obtained immediately following gelation when a strain sweep was performed from low strain to high strain; a yield strain greater than 100% is shown. The bottom line was obtained following a 10 minute relaxation period, when the strain sweep was repeated, revealing a partial recovery in complex viscosity before increased strains resulted in a repeated loss in complex viscosity.

Strain sweep analysis of the pPBA-pSHA gel at pH 4 reveals the gel is shear thinning yet is capable of recovery following time for relaxation (see FIG. 3). Longer relaxation times result in full recovery of complex viscosity.

Example 4

Self-Healing Crosslinkable Gels

Figure 4:
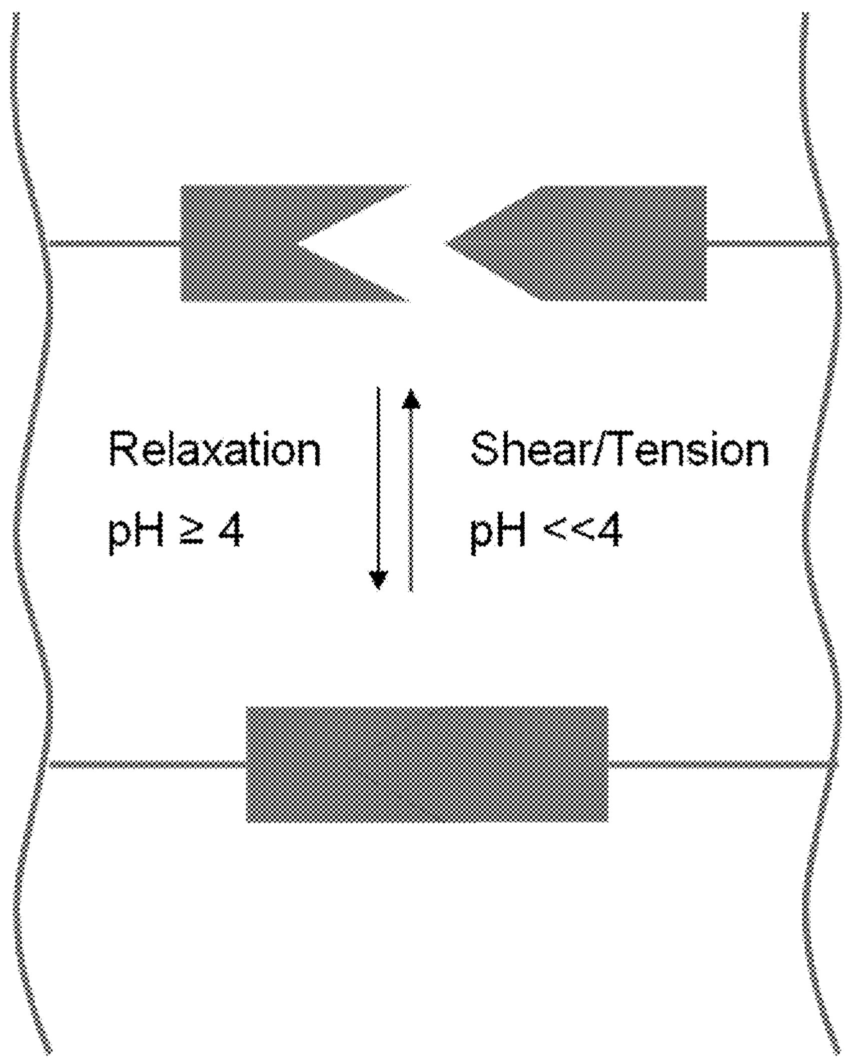
FIG. 4 is a schematic demonstrating the reversible, self-healing nature of the disclosed crosslinking polymer system.

Upon exposure to strong acid, the crosslinked gel can reverse and thus dissolve, but may re-gel when pH is increased. Upon exposure to high stresses and/or strains (either tensile or shear), the gel can break or weaken, but may re-gel when relaxed. These reversible gelation properties are rarely observed in other covalently crosslinked polymer systems (see FIG. 4).

Example 5

Gel Preparation and Dynamic Rheology

Prepolymers were individually dissolved in buffered solutions (25 mM acetate buffer, pH 4.2 or 5.5; 25 mM phosphate buffer, pH 7.6) at known polymer concentrations (50-100 mg/mL). Any pH adjustments were made using 1M NaOH or 1M HCl before final concentrations were determined.

Gels comprising p($HPMA_{90}$-$PBA_{10}$) plus p($HPMA_{90}$-$SHA_{10}$) or p($AA_{90}$-$PBA_{10}$) plus p($AA_{90}$-$SHA_{10}$) were formed in situ by simultaneously pipetting equal volumes of prepared prepolymer solutions at equal polymer concentrations (50-100 mg/mL). Dynamic rheology was performed using a cone-and-plate configuration on a stress-controlled rheometer (AR550, TA Instruments). Oscillatory frequency sweeps were performed between 0.1-100 rad/s at a controlled oscillatory stress (ranging from 1.5-50 Pa) determined from the linear viscoelastic region of oscillatory stress sweeps performed on each gel condition. Percent change in gel strength, ΔG', as a function of temperature (i.e., gel strength at 37° C. as compared to initial gel strength at 25° C.) was calculated as the difference in average G' of the quasi-plateau region (QPR) from oscillatory frequency sweeps performed at 25° C. and 37° C. Recovery of the gel post-failure was determined by inducing gel failure by at least one minute of high amplitude oscillatory stress (10,000-20,000 Pa, 10-50 rad/s) and monitoring G' recovery in oscillatory time sweeps using conditions selected from QPR (5-50 Pa, 10-50 rad/s). All experiments were performed on triplicate gel samples. The results are shown in FIG. 6A-D.

Results from the Examples

Figure 5:
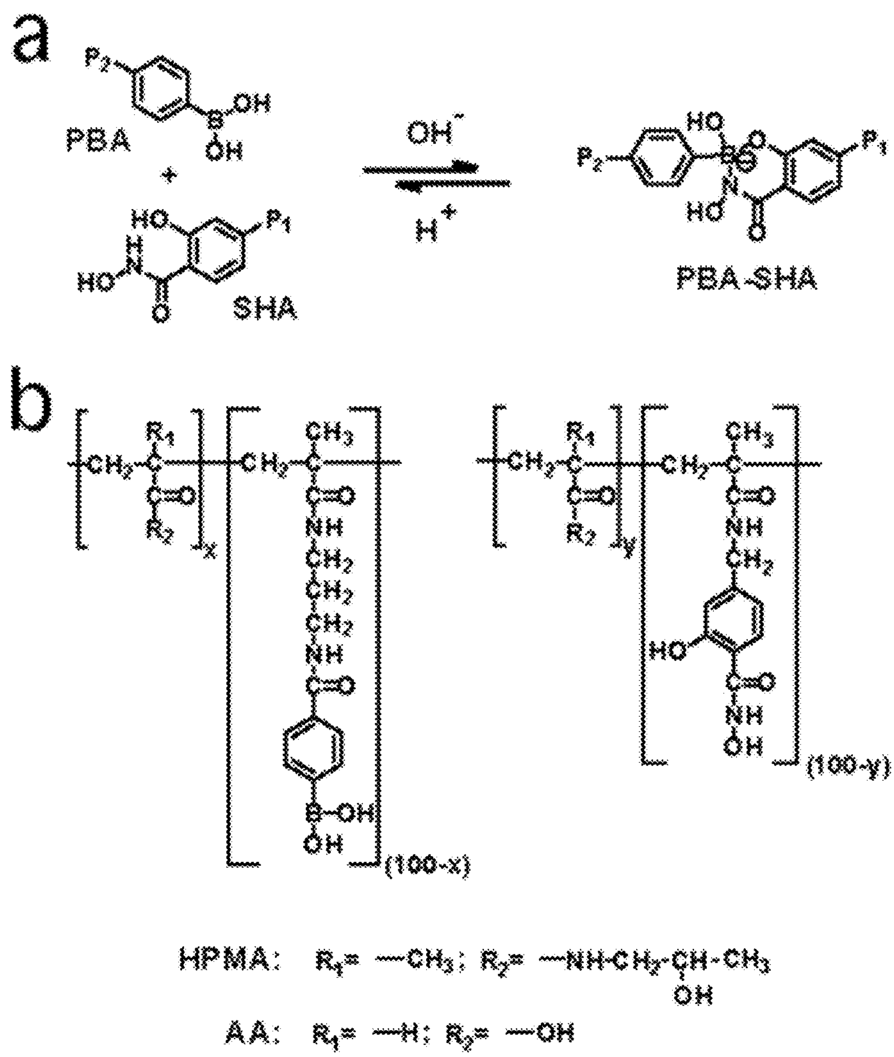
FIG. 5 is a group of schematics of self-healing, viscoelastic hydrogel networks that can be formed using reversible covalent crosslinking chemistry as disclosed herein.
Figure 5:
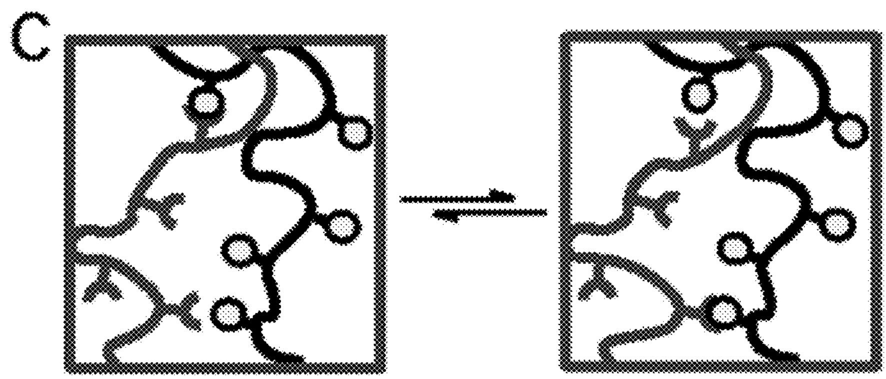

The above examples demonstrate that crosslinkable water-soluble polymers were synthesized by free radical polymerization of phenylboronic acid (PBA) or salicylhydroxamic acid (SHA) functionalized vinyl monomers (e.g., at 10 mol %) with unreactive polymer backbones (FIG. 5B). When PBA and SHA functionalized polymers are mixed as aqueous solutions at physiological pH, the PBA and SHA moieties can associate to form pH-sensitive reversible covalent bonds (Moffatt et al., *Hum Gene Ther* 16:57-67, 2005; Stolowitz et al., *Bioconj Chem* 12:229-39, 2001; Wiley et al., *Bioconj Chem* 12:240-50, 2001) (PBA-SHA, FIG. 5A), thereby generating dynamically crosslinked hydrogel networks (FIG. 5C). The dynamic viscoelasticity of PBA-SHA crosslinked hydrogels with an uncharged polymer backbone, based on 2-hydroxypropylmethacrylamide (HPMA), was evaluated at different physiologically relevant pH's (pH 4.2 and 7.6). Also, the pH range at which gels demonstrate reversible crosslinking behavior can be modified was evaluated by studying the effect a negatively-charged polymer backbone, based on acrylic acid (AA), has on the PBA-SHA crosslinked network.

Figure 8:
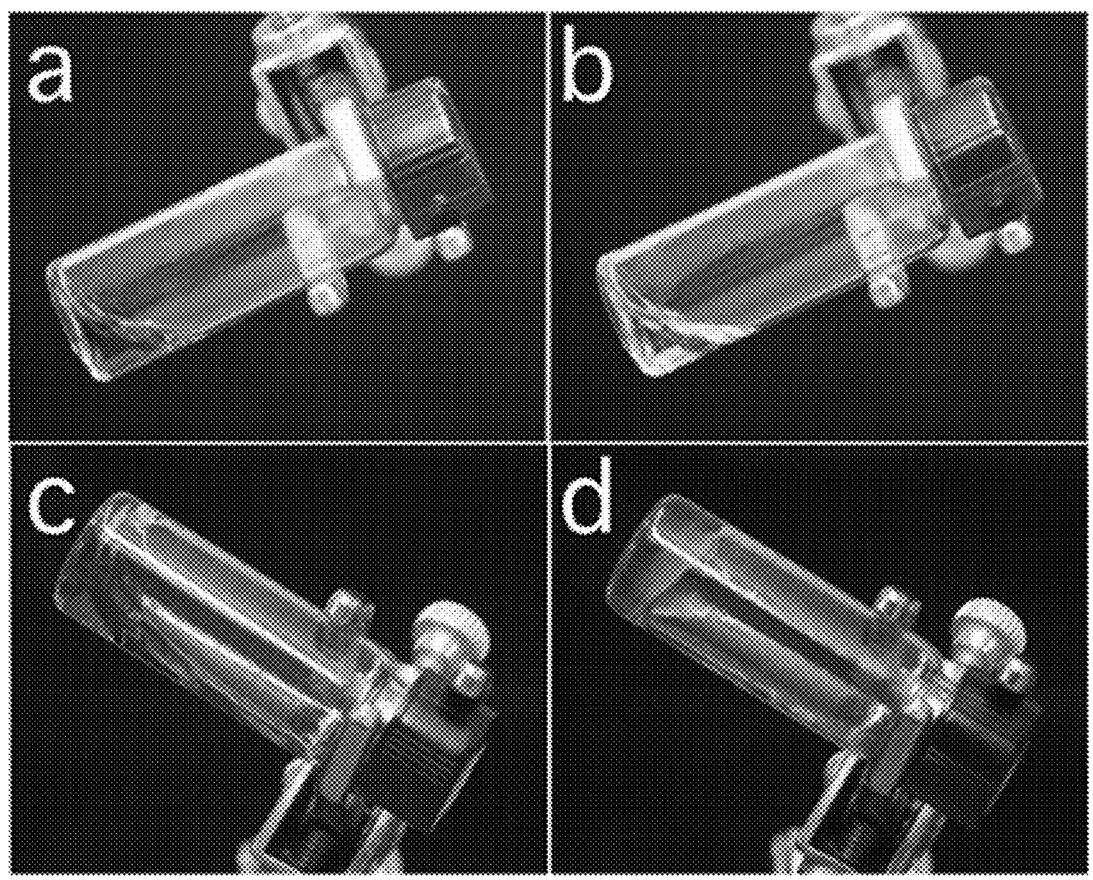
FIG. 8 is a group of four photographs showing HPMA-based PBA-SHA crosslinked hydrogels demonstrating pH-sensitive flow by gravity.

Observations of HPMA-based PBA-SHA crosslinked gels revealed a strong pH-dependence in the gel type and consistency formed from a deformable semisolid at low physiological pH to a brittle, elastic hydrogel at neutral pH. At pH 4.2 these gels demonstrate viscous-like behavior and flow by gravity on a slow time scale (FIG. 8C). These gels self-heal, or recover following mechanical disruption; rapid shearing temporarily fractures these gels into separate visible fragments that rejoin within seconds to form a single, cohesive mass. By adding 1-2 equivalents of a small molecule SHA derivative to the mixture or by reducing the pH to 2, the gel formation can be inhibited, reducing the viscosity. While not wishing to be bound by theory, such results indicate that the viscous behavior of these gels results from the PBA-SHA interactions, whose binding equilibrium is shifted toward the unbound monomers state at pH 4.2, allowing for constant restructuring of the few reversible crosslinks in the gel network (FIG. 5B-C). Furthermore, these gels exhibit spinnbarkeit behavior similar to cervical mucus, i.e., the ability to stretch into thread-like dimensions. In fact, these gels could be stretched into string-like dimensions nearly 1 m in length.

At pH 7.6, where the crosslinking equilibrium is nearly totally shifted toward the PBA-SHA bound state, the HPMA-based gels do not flow when inverted (FIG. 8D) and are brittle, similar to typical covalent gel networks. Moreover, these gels remain fractured for days after mechanical tearing.

AA-based PBA-SHA crosslinked gels at pH 7.6 have a self-healing, dynamic nature similar to HPMA-based gels at pH 4.2. These gels demonstrate gravity-induced flow, rapid recovery post-fracturing and spinnbarkeit behavior. The polymer backbone-induced shift in gel reversibility to a higher pH is likely due to an altered binding equilibrium by the Donnan effect, increasing the acidic microenvironment local to the PBA-SHA crosslinks, or other electrostatic or hydrogen bonding effects that may be present between the polymer chains. These combined observations demonstrate the ability to engineer a range of gel properties with the PBA-SHA crosslinked hydrogel system at varying physiological pH's, from a dynamic self-healing semisolid gel to a covalent, highly crosslinked hydrogel network.

Gel behavior was quantified by subjecting the PBA-SHA crosslinked hydrogels to dynamic rheology as a function of angular frequency. Typically, gels formed with permanent covalent bonds demonstrate frequency-independent elastic (G') and viscous (G") moduli with G'>G", whereas gels formed with temporary, reversible bonds are known to display frequency-dependent moduli (Franse, *Polymer Materials and Engineering* 142, 2002; Goodwin and Hughes, *Rheology for Chemists: An Introduction,* 2000). At low angular frequencies fluid-like behavior dominates in reversible gels (i.e., G'<G") because the time scale probed in the experiment is sufficiently longer than the lifetime of the kinetically labile crosslinks, allowing time for the network to restructure under stress. At higher angular frequencies, where not enough time is provided for the labile crosslinks to dissociate, elastic-like behavior dominates (G'>G") and G' becomes independent (i.e., quasi-plateau) at these higher frequencies.

Figure 6:
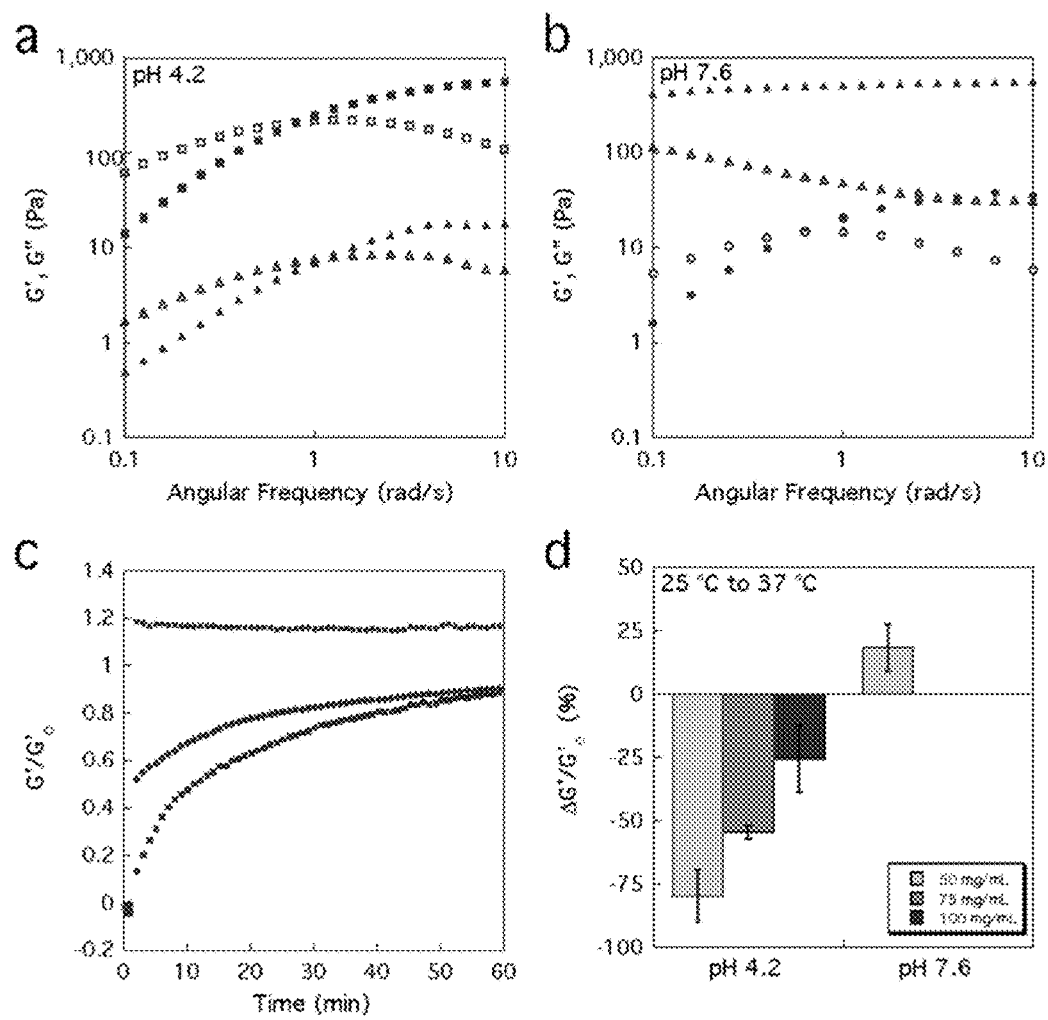
FIG. 6 is a group of four graphs showing results of the Dynamic rheology of PBA-SHA crosslinked hydrogels.
Figure 7:
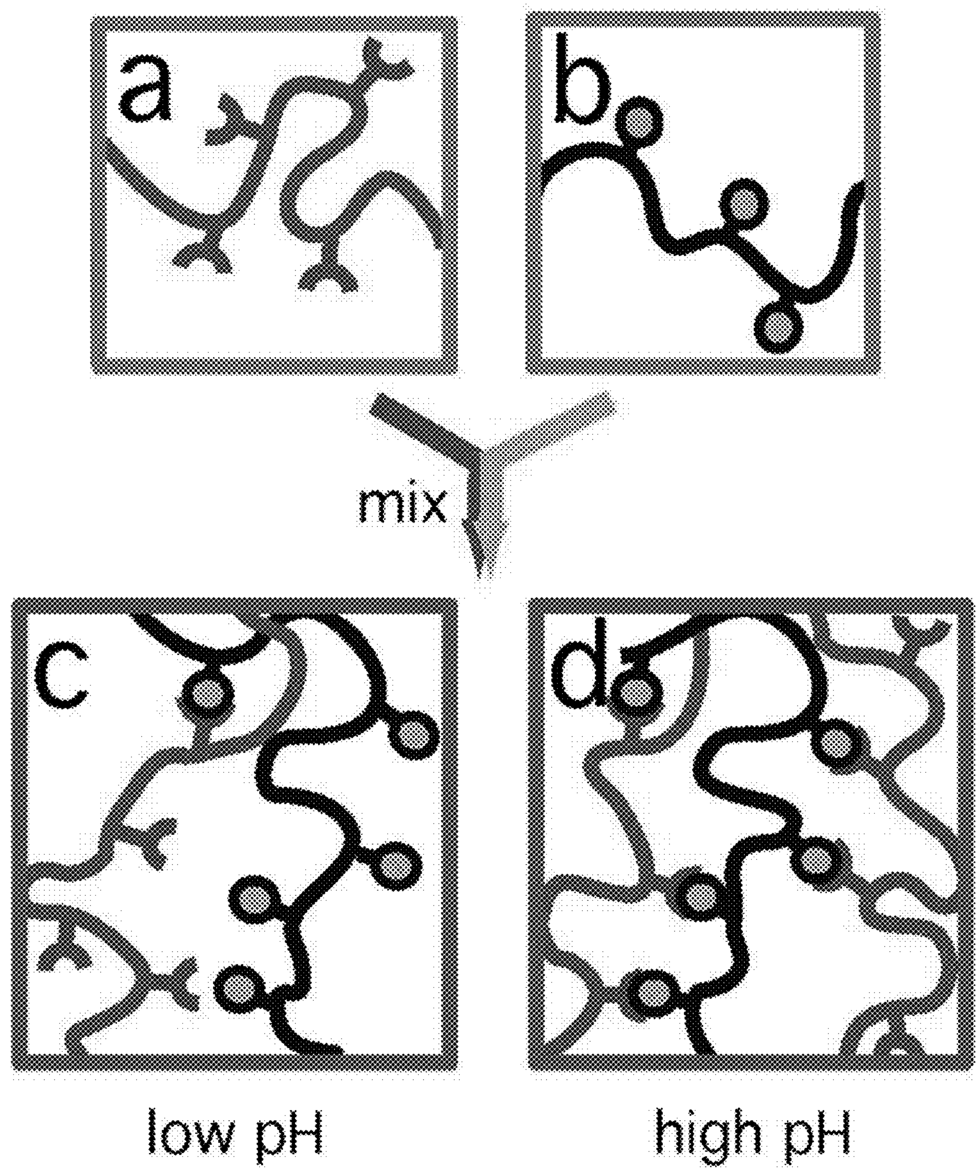
FIG. 7 is a schematic of in situ gelling polymer hydrogel networks using reversible PBA-SHA covalent crosslinking chemistry. When SHA-functionalised polymers (a) are mixed with PBA-functionalised polymers (b) under physiological conditions, a dynamic semisolid gel forms at low pH (c) due to the presence of reversible crosslinks. At higher pH's (d), the binding equilibrium of the covalent crosslinks is shifted toward a more irreversibly bound state and a highly crosslinked hydrogel results.

Results from the HPMA-based PBA-SHA crosslinked gels at pH 4.2 and AA-based PBA-SHA crosslinked gels at pH 7.6 subjected to oscillatory frequency sweeps are consistent with the rheological properties of reversible gels. For these gels at all polymer concentrations tested, G" dominates G' at angular frequencies below approximately 1 rad/s, at which point G' crosses over G" and plateaus above approximately at higher angular frequencies (FIGS. 6A and 6B). For HPMA-based gels at pH 7.6, however, G' dominates G" over the same experimental range (FIG. 6B), demonstrating that the gel now behaves similar to those of a typical permanently crosslinked network. The observed transition of the HPMA-based PBA-SHA crosslinked gels from a dynamic semisolid state in an acidic environment to an irreversibly crosslinked state in a neutral environment occurs due to a pH-induced increase in the lifetime, or rightward shift in the binding equilibrium, of the reversible, coordinate covalent bond. Furthermore, by adding negative charges to the PBA-SHA crosslinked polymer system, as in the case with the AA-based gels, the crosslinker's sensitivity to pH can be adjusted and thus one can control the gel reversibility over a broad pH range.

PBA-SHA crosslinked gels show reversible behavior at the molecular scale, and the HPMA-based gels at pH 4.2 and AA-based gels at pH 7.6 are expected to recover their original mechanical properties after being stressed to the point of gel failure (Nowak et al., *Nature* 417:424-28, 2002). The gels were subjected to a large amplitude deformation (>10,000 Pa oscillatory stress) followed by an oscillatory time sweep under small amplitude deformation conditions (<50 Pa oscillatory stress). HPMA-based PBA-SHA crosslinked gels at pH 4.2 and AA-based PBA-SHA crosslinked gels at pH 7.6 displayed a concentration-dependent recovery of G' in time following failure (FIG. 6C), while HPMA-based gels at pH 7.6 were not observed to recover post-failure. These data suggest that the pH 4.2 HPMA-based gels and pH 7.6 AA-based gels restructure by crosslink reassociation after stress, while pH 7.6 HPMA-based gels permanently fracture between crosslinks and are thus not able to restructure.

PBA-SHA crosslinked gels also demonstrate temperature-sensitive viscoelastic behavior. Slight rises in temperature (i.e., from 25° C. to 37° C.) result in diminished gel strength for dynamic semisolid gels, such as the HPMA-based gels at pH 4.2 (FIG. 6D). This temperature dependence of gel strength demonstrates the thermodynamic sensitivity of these gels with labile crosslinks. HPMA-based gels at pH 7.6 that are highly and more irreversibly crosslinked, however, do not demonstrate the same temperature increase induced loss in gel strength but rather reveal a slight increase in gel strength (FIG. 6D). While not wishing to be bound by theory, this suggests that a much larger temperature increase is necessary to effect the thermodynamics of the highly crosslinked PBA-SHA hydrogel networks. These temperature- and pH-dependent viscoelastic properties are useful in processing of PBA-SHA crosslinked hydrogels as well as in the development of smart biomaterials with physiologically triggerable structural transformations.

The rheological properties of PBA-SHA crosslinked hydrogels can be further engineered by modifying polymer concentration and degree of substitution of the crosslinking moieties. Increasing the polymer concentration of HPMA-based gels results in an increased gel strength (FIG. 6A), due to an increase in crosslink density, at all pH's tested. This polymer concentration-dependent change in gel strength, however, does not alter the reversible/irreversible nature of the gel (FIG. 6A), because the lifetime of the crosslink as well as the molecular weight between crosslinks is unaffected by increased polymer concentration at a given pH. Decreasing the degree of substitution of the crosslinking moieties while holding the polymer concentration constant results in weaker dynamic semisolid gels, such as the HPMA-based gels at pH 4.2, whereas the gel strength of highly crosslinked HPMA-based gels at pH 7.6 remain unaffected. This selective effect of degree of substitution on gel strength for HPMA based PBA-SHA crosslinked semisolids, combined with the non-selective effect of polymer concentration on gel strength for all PBA-SHA crosslinked networks, allows the disclosed compositions to be used in pH-triggerable materials for which changes in gel strength may or may not be desired.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A polymeric gel composition comprising a first polymer comprising at least two boronic acid moieties, and a second polymer comprising at least two hydroxamic acid moieties, wherein the first polymer and the second polymer are reversibly crosslinked by reaction between at least one of the boronic acid moieties and at least one of the hydroxamic acid moieties.

2. The composition of claim 1, wherein the boronic acid moiety comprises Formula IV:

IV

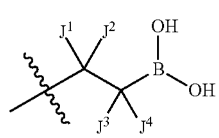

where $J^{1-4}$ are independently selected from the group consisting of hydrogen, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol.

3. The composition of claim 1, wherein the boronic acid moiety comprises a moiety having Formula V:

V

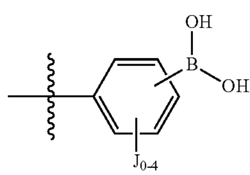

where each J is independently selected from the group consisting of substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol.

4. The composition of claim 1, wherein the hydroxamic acid moiety comprises Formula VI:

VI

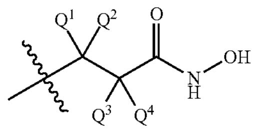

where $Q^{1-4}$ are independently selected from the group consisting of hydrogen, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol.

5. The composition of claim 1, wherein the hydroxamic acid moiety comprises a phenylhydroxamic acid moiety having Formula VII:

VII

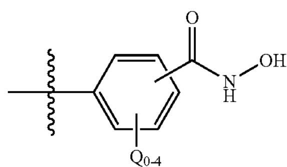

where each Q is independently selected from the group consisting of substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, azide, nitro, silyl, sulfo-oxo, and thiol.

6. The composition of claim 1, wherein the hydroxamic acid moiety comprises a phenylhydroxamic acid moiety having Formula VIIIa:

VIIIa

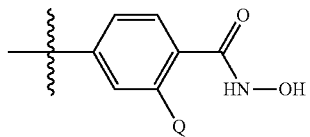

where Q is hydroxy, alkoxy, nitro, amino, or halide.

7. The composition of claim 1, wherein the arylhydroxamic acid moiety comprises a phenylhydroxamic acid moiety having Formula VIIIb:

VIIIb

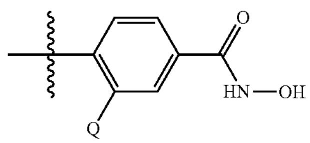

where Q is hydroxy, alkoxy, nitro, amino, or halide.

8. A polymeric gel composition prepared by contacting a first polymer comprising one or more hydroxamic acid moieties and a second polymer comprising one or more boronic acid moieties under conditions where the hydroxamic acid and boronic acid moieties undergo a reaction to provide a boronate ester.

9. A pharmaceutical composition comprising a bioactive agent and the polymeric gel composition of claim 1.

10. The pharmaceutical composition of claim 9, wherein the bioactive compound comprises a growth factor, an anti-inflammatory agent, an anti-cancer agent, an analgesic, an anti-infection agent, an anti-cell attachment agent, an anti-viral agent, a hormone, an antibody, or a therapeutic protein.

11. The pharmaceutical composition of claim 9, wherein the bioactive agent comprises a microbicide, a spermicide, an anti-inflammatory agent, or mixture thereof.

12. The composition of claim 1, wherein the composition is contained in or coated on a vaginal device.

13. The composition of claim 12, wherein vaginal device comprises a vaginal tampon, vaginal ring, vaginal strip, vaginal capsule, vaginal tablet, vaginal pessary, vaginal cup, vaginal film, or vaginal sponge.

14. The composition of claim 1, wherein the composition is applied to vaginal mucosa in the form of a cream, lotion, or foam.

15. The composition of claim 1, wherein the boronic acid moiety is an arylboronic acid moiety.

16. The composition of claim 1, wherein the hydroxamic acid moiety is an arylhydroxamic acid.

17. The composition of claim 1, wherein the hydroxamic acid moiety is a salicylhydroxamic acid.

18. The composition of claim 1, wherein at least one of the polymers was synthesized by free radical polymerization of phenylboronic acid (PBA) functionalized vinyl monomers or salicylhydroxamic acid (SHA) functionalized vinyl monomers, optionally with co-monomers based upon acrylic acid.

19. The composition of claim 1, wherein the polymeric gel has a molecular weight of from about 2,000 Da to about 2,000,000 Da.

20. The composition of claim 1, wherein the boronic acid moiety is an arylboronic acid moiety, wherein the hydroxamic acid moiety is an arylhydroxamic acid, and wherein the polymeric gel has a molecular weight of from about 2,000 Da to about 2,000,000 Da, and wherein the polymeric gel composition comprises a hydrogel network at physiological pH.

21. The composition of claim 1, wherein the polymeric gel composition comprises a hydrogel network at acidic pH, wherein the hydrogel viscosity increases when exposed to a more basic pH.

22. The composition of claim 21, wherein the composition is contained in or coated on a vaginal device, or the composition is applied to vaginal mucosa in the form of a cream, lotion, or foam.

23. The composition of claim 21, further comprising a bioactive agent.

24. The composition of claim 21, wherein the bioactive agent is selected from microbicides, spermacides, and anti-inflammatory agents.

* * * * *